United States Patent [19]
Serrero

[11] Patent Number: 5,846,734
[45] Date of Patent: Dec. 8, 1998

[54] MAMMALIAN ADIPOGENIC FACTORS

[75] Inventor: Ginette Serrero, Lake Placid, N.Y.

[73] Assignee: W. Alton Jones Cell Science Center, Lake Placid, N.Y.

[21] Appl. No.: 485,795

[22] Filed: Jun. 7, 1995

Related U.S. Application Data

[62] Division of Ser. No. 215,673, Mar. 22, 1994, Pat. No. 5,449,757, which is a continuation of Ser. No. 824,847, Jan. 17, 1992, abandoned, which is a continuation-in-part of Ser. No. 531,393, Jun. 1, 1990, abandoned.

[51] Int. Cl.⁶ .............................. G01N 33/53; C12Q 1/32; C12Q 1/02
[52] U.S. Cl. ................................. 435/7.1; 435/26; 435/29
[58] Field of Search .......................... 435/7.1, 7.9, 7.92, 435/7.2, 26, 29; 436/501, 518, 536, 811

[56] References Cited

U.S. PATENT DOCUMENTS 5,039,619  8/1991  Staple et al. .

OTHER PUBLICATIONS

Serrero et al., "Differentiation of Newborn Rad Adipocyte Precursors in Defined Serum–free Medium", In Vitro Cell. Dev. Biol. 22, 63–66, 1987.
Swierczewski et al., "Characterization of rat preadipocytes from normal rat adipose tissue by their effector response", Biochem. J. 248, 383–387. 1987.
Flores–Delgado et al., "Thyroid hormone stimulates adipocyte differentiation of 3T3 cells", Mol. Cell. Biochem. 76, 35–43, 1987.
Kawashima et al., "Interleukin–11: A Novel Stroma–derived Cytokine", Progr. Growth Factor Res. 4, 191–206, 1992.
James Darnell et al., "Molecular Cell Biology," Scientific American Books, pp. 221–222, 260–262.
Gaillard et al., Biochim. Biophys. Acta., vol. 846, pp. 185–191, 1985.
C. Milstein et al., "Continous cultures of fused cells secreting antibody of predefined specificity," Nature, vol. 26, Aug. 7, 1975.
Zaitsu et al., J. Cellular Physiology, vol. 485–491 and vol. 49. pp. 339–346, 1991.

*Primary Examiner*—Paula K. Hutzell
*Assistant Examiner*—Donna C. Wortman
*Attorney, Agent, or Firm*—Browdy and Neimark

[57] ABSTRACT

Mammalian adipogenic factors, including purified proteins or glycoproteins, capable of inducing the adipose differentiation of adipogenic cells are disclosed, as are antibodies to such proteins, DNA encoding the proteins and host cells expressing the proteins. A method for determining the susceptibility of a subject to obesity by measuring the levels of one or more adipogenic factors in a biological fluid or tissue extract is also disclosed, as is a method for evaluating an anti-obesity drug which comprises contacting the drug with cells capable of producing one or more adipogenic factors and measuring the amount of the factors produced.

2 Claims, 12 Drawing Sheets

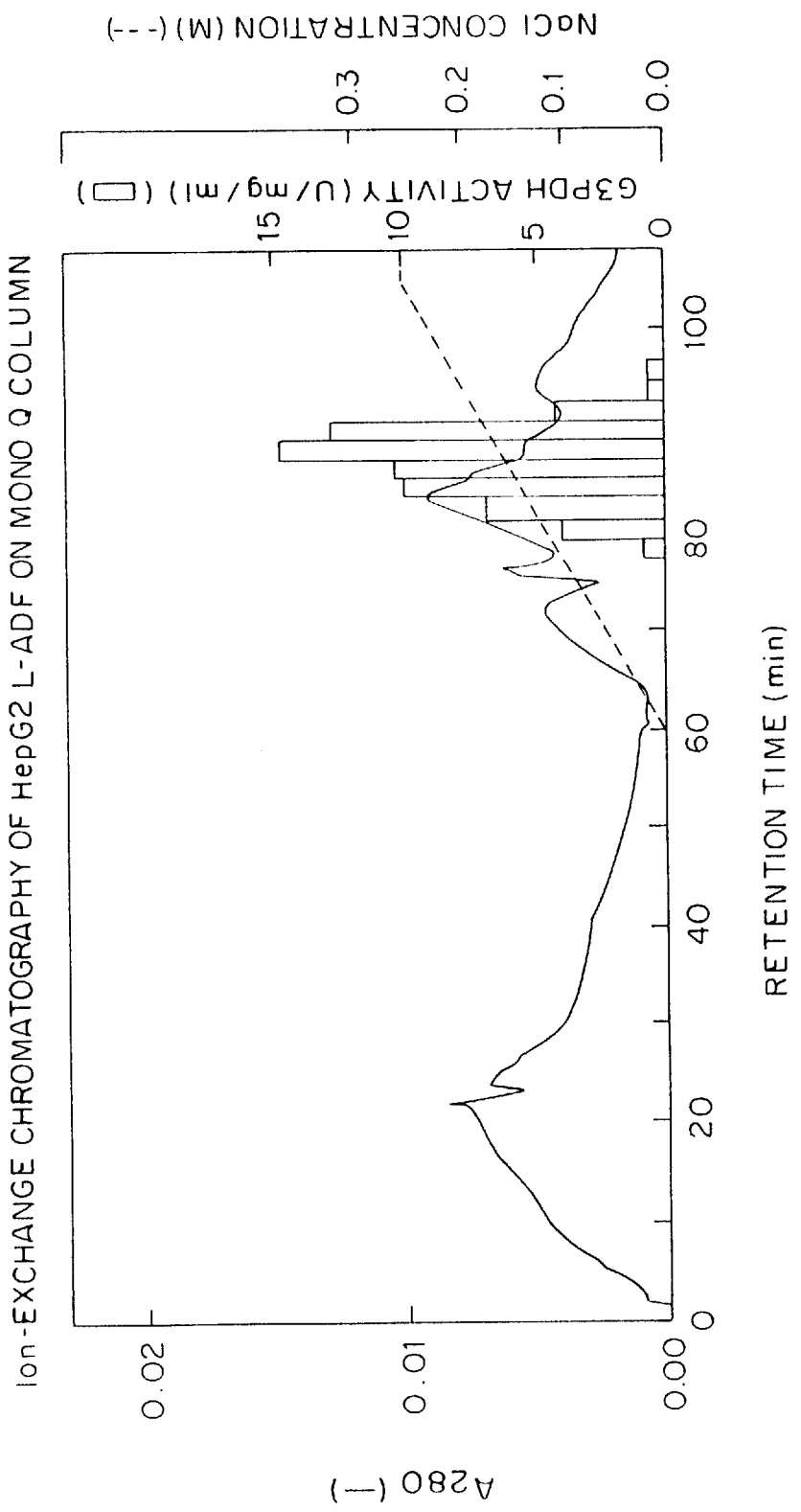

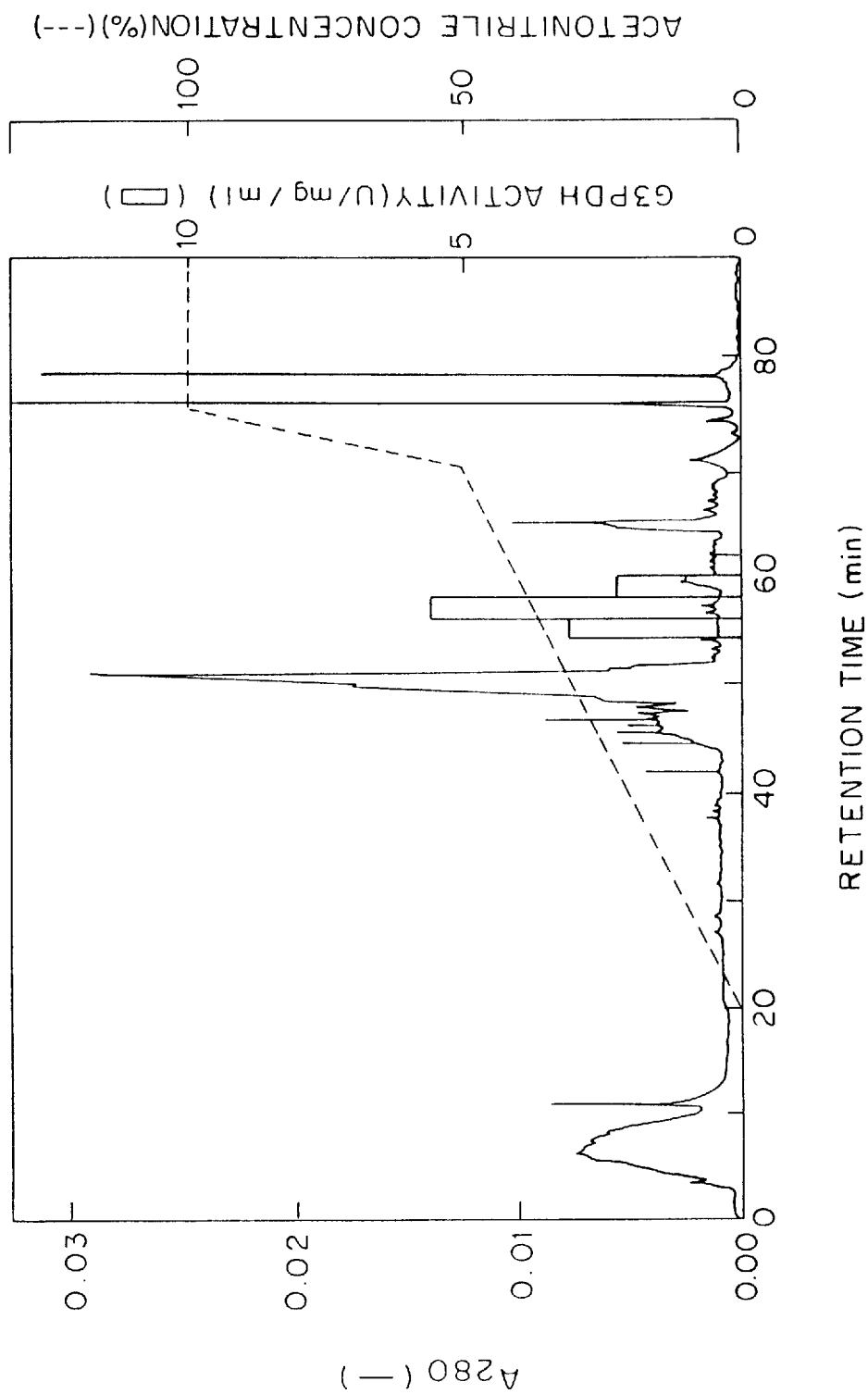

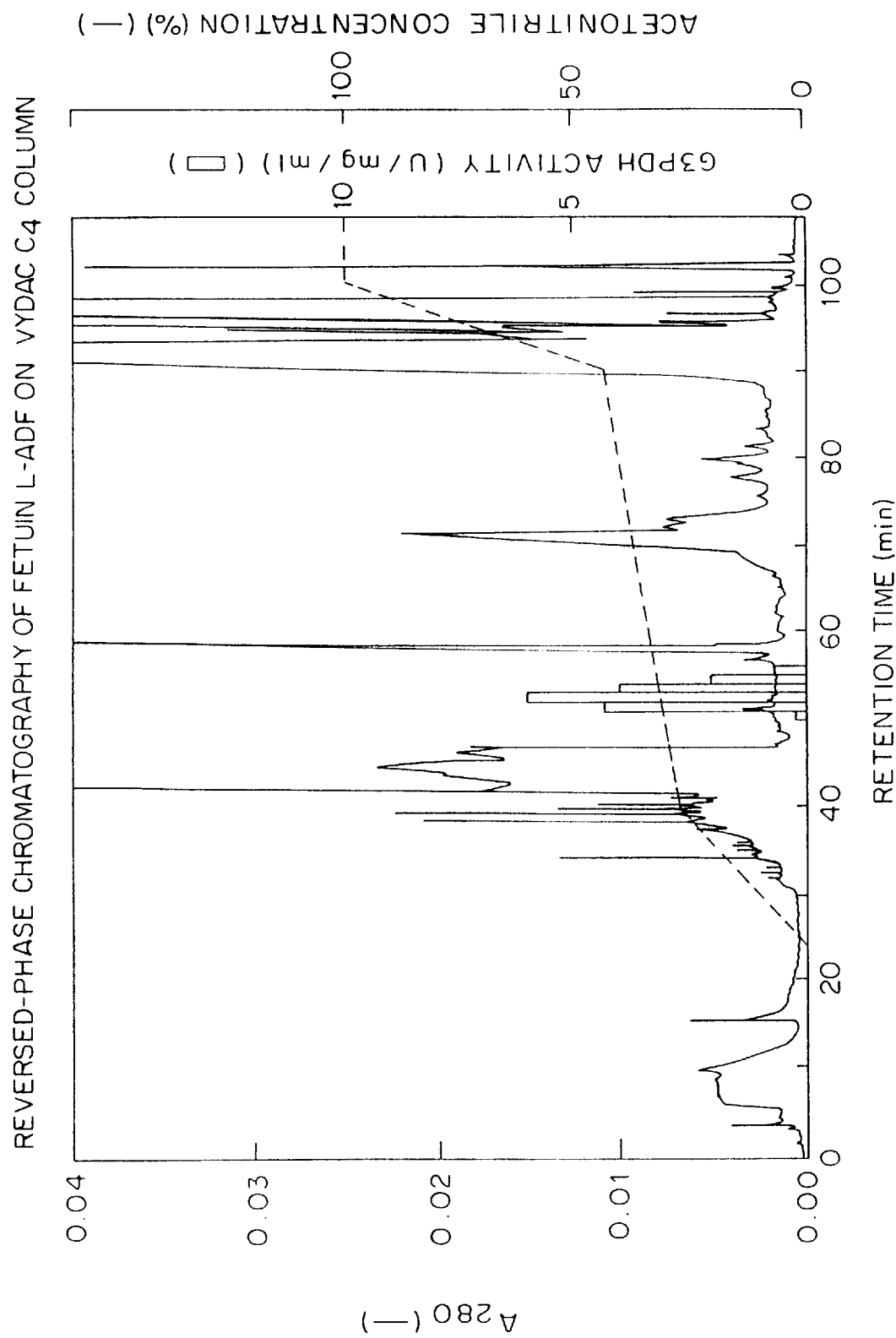
FIG. 12 REVERSED-PHASE CHROMATOGRAPHY OF FETUIN L-ADF ON VYDAC C4 COLUMN

MAMMALIAN ADIPOGENIC FACTORS

CROSS-REFERENCE TO RELATED APPLICATIONS

The present application is a divisional of U.S. application Ser. No. 08/215,673, filed Mar. 22, 1994, now U.S. Pat. No. 5,449,757 which is a continuation of U.S. application Ser. No. 07/824,847, filed Jan. 17, 1992, now abandoned, which is a continuation-in-part of U.S. application Ser. No. 07/531,393, filed Jun. 1, 1990, now abandoned.

BACKGROUND OF THE INVENTION

1. Field of the Invention

The invention in the field of cell biology, physiology and medicine relates to purified mammalian adipogenic proteins, genetic constructs thereof, antibodies thereto, and methods of using such factors to determine susceptibility to obesity and for evaluating efficacy of anti-obesity drugs.

2. Description of the Background Art

Adipose differentiation of adipogenic cell lines is under the control of protein or glycoprotein factors called "adipogenic factors" which either trigger or stimulate the process of adipose differentiation. The isolation and complete identification of adipogenic factors is important because of their role in turning on the differentiation program. Reports in the literature have disclosed that abnormal levels of circulating adipogenic factors exist in the blood of obese individuals (Lau, D. C. W. et al., (1984) *Proc. 7th International Congress Endocrinology Excerpta Medica*, p. 866).

Adipogenic factors have been found in fetal bovine serum and in human serum and plasma. Crude fetuin preparations have been shown to possess adipogenic activity that is heat sensitive and acid (pH 1) sensitive. The adipogenic activity was attributed to the fetuin itself (Gaillard, D. et al. (1985) *Biochem. Biophys. Acta* 846:185–191). There have been additional reports of bovine or human serum or plasma factors which provided little or no characterization of the physico-chemical properties of the factors (Meada, Y. Y. et al. (1980) *Exp. Cell. Res.* 126:99–107; Kuri-Harcuch, W. et al., (1978) *Proc. Natl. Acad. Sci. U.S.A.* 75:6107–6109; Serrero, G. et al. (1979), In: *Hormone and Cell Culture*, Cold Spring Harbor Conference on Cell Proliferation, Vol. 6, (R. Ross et al., eds.), Cold Spring Harbor Laboratory Press, Cold Spring Harbor, N.Y.); D. Gaillard et al. (1984) *In Vitro Cell. Dev. Biol.* 20:79–88; and G. Sypniewska et al. (1986) *Int. J. Obesity* 10:265–276).

Aproliferin, a factor purified from human plasma, is a 45 kDa protein (Weir, M. L. et al., *Am. J. Physiol.* (1982) 125:546–554) which induces loss of proliferative potential of 3T3-T proadipocytes. Based on its molecular weight and mode of action (Grimaldi, P. et al. (1982) *EMBO J.* 1:687–692), aproliferin is distinct from the adipogenic factors of the present invention. A heat labile, acid stable and protease stable active fraction has also been isolated from fetal calf serum (Grimaldi et al., supra). It appears likely that the active component is arachidonic acid, a fatty acid (Gaillard, D. et al. (1989) *Biochem. J.* 257:389–397).

SUMMARY OF THE INVENTION

The present invention is directed to novel mammalian, including human, adipogenic proteins or glycoproteins. These adipogenic factors which appear to play an important role in the generation of fat cells in mammals, are useful in a method for determining the susceptibility of a subject to obesity. Antibodies to the adipogenic factors are also useful in this regard. The adipogenic factors have additional utility in evaluating the efficacy of anti-obesity drugs or therapies.

The present invention is directed to a mammalian liver cell-derived adipogenic factor comprising an adipogenic protein having an apparent molecular weight of about 50 kDa, or an aggregate or complex of the protein, the factor being of sufficient purity such that its adipogenic activity per milligram protein is at least 625 times that of an extract or conditioned medium of liver cells from which it is obtained. Preferably, this factor is the adipogenic protein or glycoprotein having an apparent molecular weight of about 50 kDa substantially free of other proteins or glycoproteins with which it is natively associated.

The carrier proteins with which the adipogenic factor may be complexed include α2-macroglobulin, albumin, and lipoproteins.

Preferably, the adipogenic factor is of human origin. The adipogenic factor or purified adipogenic protein may be derived from a cultured hepatocyte or hepatocyte tumor cell line, most preferably, from the HepG2 cell line.

In one embodiment, the above adipogenic protein or glycoprotein is prepared by the steps of:
  (a) obtaining the conditioned medium of the cells and concentrating the conditioned medium about 25- to about 40-fold;
  (b) subjecting the concentrated material obtained in step (a) to heparin-SEPHAROSE as heparin-beaded agarose chromatography at neutral pH and eluting the bound material with a salt at a concentration of about 1 molar;
  (c) solubilizing the eluate of step (b) with a non-ionic or non-denaturing zwitterionic detergent to dissociate any aggregates or complexes of the adipogenic protein;
  (d) subjecting the solubilized material obtained in step (c) to size-exclusion chromatography and collecting the material having a molecular weight of about 50 kDa;
  (e) subjecting the material obtained in step (d) to anion exchange chromatography at neutral pH and eluting with a salt gradient; and
  (f) subjecting the eluate of step (e) to reverse-phase HPLC and eluting with a gradient of a nonpolar organic solvent in the presence of an ion-pairing agent.

Preferably, the salt in step (b) is NaCl, the detergent in step (c) is n-octyl,β-D-glucopyranoside or 3-[(3-cholamidopropyl)dimethylammonio]-1-propane sulfonate, the size-exclusion chromatography is with a SEPHACRYL-S-300 of a cross-linked copolymer of allyl dextran and N,N-methylene bisacrylamide having a fractionation range for globular proteins of $1\times10^4$–$1\times10^6$, the anion exchange chromatography is with a MONO Q Column of a monodisperse, beaded hydrophilic resin matrix gel having quaternary amine groups, the salt gradient of step (e) is 0 to 5M NaCl, the gradient of step (f) is 0–50% acetonitrile, and the ion pairing agent is 0.1% trifluoroacetate.

In another embodiment, the present invention provides a mammalian serum-derived adipogenic factor comprising an adipogenic protein having an apparent molecular weight of about 34 kDa, a pI of 9.6, and stability to a pH of between about 4.0 and 8.0, or an aggregate or complex of the adipogenic protein, the factor being of sufficient purity such that its adipogenic activity per milligram protein is at least about 250 times that of the adipogenic activity of whole serum or of crude fetuin.

In the complexed form, the carrier protein is preferably α2-macroglobulin or acidic glycoprotein fetuin.

Preferably, the adipogenic factor is an adipogenic protein having an apparent molecular weight of about 34 kDa, an isoelectric point of pI=9.6, and stability to a pH between about 4.0 and 8.0, substantially free of other proteins or glycoproteins with which it is natively associated.

The serum-derived adipogenic factor or protein is preferably of bovine or human origin. In one embodiment, the protein is isolated from crude bovine fetuin.

Preferably, the serum-derived adipogenic protein or glycoprotein is prepared by the steps of:

(a) suspending, dissolving or dialyzing crude fetuin into a chromatofocusing buffer;

(b) chromatofocusing the material obtained in step (a) on a chromatofocusing column which has been equilibrated with the buffer of step (a), and collecting the unbound flow-through fraction;

(c) solubilizing the flow through fraction with a non-ionic or non-denaturing zwitterionic detergent to dissociate any aggregates or complexes of the adipogenic protein;

(d) subjecting the solubilized flow through fraction obtained in step (c) to cation exchange chromatography and eluting with a salt gradient;

(e) subjecting the eluate of step (d) to reverse-phase HPLC and eluting with a gradient of a nonpolar organic solvent in the presence of an ion-pairing agent.

Preferably, the buffer in step (a) is a 25 mM imidazole-HCl buffer, pH 8.0, the chromatofocusing column of step (b) is a polybuffer exchanger column, the detergent of step (c) is n-octyl,β-D-glucopyranoside or 3-[(3-cholamidopropyl) dimethylammonio]-1-propane sulfonate, the cation exchange chromatography is with an S-SEPHAROSE column, the salt gradient of step (d) is 0 to 0.2M NaCl, the gradient of step (e) is 0–50% acetonitrile, and the ion pairing agent is 0.1% trifluoroacetate.

The invention is further directed to polynucleotide molecules, in particular DNA, which encode the liver-derived or serum-derived adipogenic protein, the DNA molecule being substantially free of nucleotide sequences encoding proteins with which the adipogenic protein is natively associated. Also included are expression vectors comprising the DNA encoding the adipogenic protein, and prokaryotic and eukaryotic host cells transformed or transfected by, and capable of expressing, this DNA.

Also provided is an antibody, either polyclonal or monoclonal, specific for an adipogenic protein or aggregated or complexed adipogenic factor, as above. Such antibodies are useful both in isolation and purification of the factors as well as in the methods of the invention directed to evaluating anti-obesity drugs or in determining susceptibility to obesity. The antibodies are also useful in methods for treating obesity wherein an antibody to an adipogenic factor is administered to a subject who is susceptible to obesity based on increased levels of the adipogenic factor.

The present invention provides a method for determining the susceptibility of a subject to obesity which comprises removing a sample of a biological fluid or tissue from the subject and measuring the amount of an adipogenic factor or adipogenic protein, as above, in the fluid or tissue, the amount of the protein or factor being proportional to the susceptibility.

Also included is a method for evaluating the efficacy of an anti-obesity drug which comprises contacting the drug with an adipogenic cell in vitro and measuring the amount of the above adipogenic factor or protein produced by the cell.

BRIEF DESCRIPTION OF THE DRAWINGS

FIG. 4 shows the results of ion-exchange chromatography of HepG2 L-AF on a MONO Q Column FIG. 5 shows the results of reversed-phase HPLC of HepG2 L-AF on a VYDAC C4 Column

FIG. 12 shows results of Reversed-Phase HPLC of Fetuin L-AF on a VYDAC C4 Column.

DESCRIPTION OF THE PREFERRED EMBODIMENTS

Figure 1:
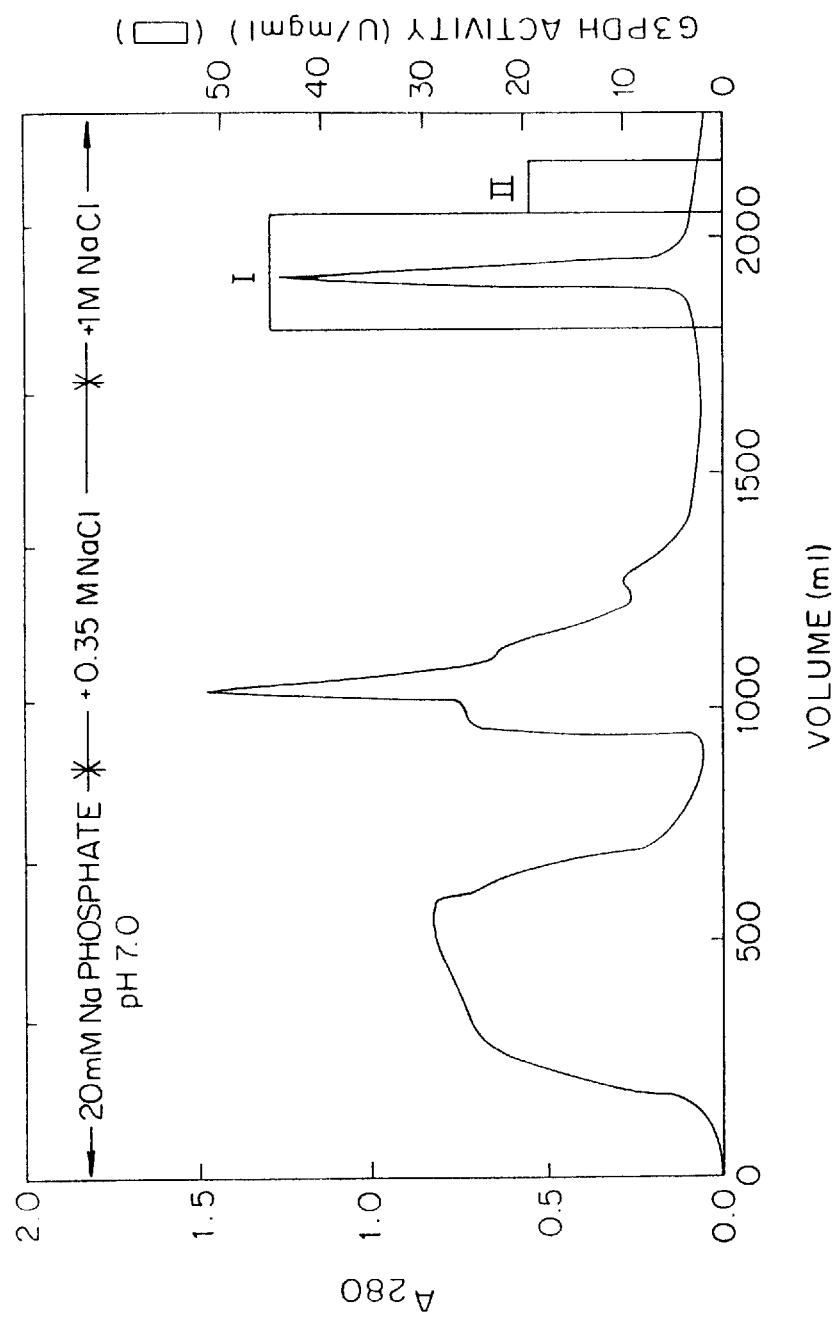
FIG. 1 shows results of heparin-SEPHAROSE chromatography of the 30–50% ammonium sulfate fraction of HepG2-derived human adipogenic factor preparation. This fraction (195 ml) was diluted with ultrapure water to adjust the conductivity to 15 mS/cm (15 mmho) and applied to a heparin-SEPHAROSE CL-6B column (4.2×20 cm) using 20 mM sodium phosphate buffer, pH 7.0. The column was washed with the same buffer and subsequently with the same buffer containing 0.35M NaCl at flow rate of 120 ml/h. Adipogenic activity was eluted with the same buffer containing 1M NaCl at flow rate of 50 ml/h. The activity was separated into two fractions, denoted fraction I and II.

The inventors have discovered and purified human and bovine adipogenic factors and have isolated one human and two bovine adipogenic proteins (or glycoproteins).

The use of the adipogenic cell line, 1246, which can be maintained in defined medium, and the use of fetuin as the starting material were the keys for purification of the bovine factors. Moreover, the use of 1246 cells has allowed the characterization of the human factor, since these cells, for proliferation, require only small amounts of the growth factors which are present in the fetuin but absent in human HepG2 conditioned medium (CM), a preferred source of the human factor; other adipogenic cell lines (such as 3T3-L1 and Ob17) require greater amounts of the growth factors not found in conditioned medium (CM) of HepG2 cells, a human hepatocyte-like cell line (Knowles, B. B. et al. *Science* 209:497–499 (1980)), rendering the bioassay for the adipogenic protein in these latter cell lines more difficult to interpret.

For isolation and characterization of the adipogenic factor or protein, a bioassay measuring the induction of glycerol-3-phosphate dehydrogenase (G3PDH) during adipose differentiation is utilized (L. Wise and H. Green (1979) *J. Biol. Chem.*, 254, 273–275). The induction of this enzyme is extremely powerful (>100 fold), easy to measure, and is correlated with the degree of cell differentiation. Other parameters that can be measured to assess adipogenic protein activity include the amount of triglyceride accumulated per cell and the "frequency" of differentiation (represented by the proportion of differentiated adipocytes of the total number of cells.)

Using the bioassay, the inventors discovered that an adipogenic protein is produced by normal rat hepatocytes in culture. That resulted in the identification of liver cells as the physiological source of the adipogenic factor in vivo, a discovery important for the subsequent discovery of the human adipogenic protein in the supernatant of the human hepatocyte-like cell line, HepG2. Additionally, a bovine adipogenic protein was isolated from fetuin, a bovine serum substitute known to stimulate proliferation and various functions in several different types of cells in vitro (D. Salomon et al. (1984), in *Cell Culture Methods for Molecular and Cell Biology, Vol 3*, D. W. Barnes et al., Eds., Alan R. Liss Inc., New York, pp 125–153.)

The term "mammalian adipogenic factor" refers to a molecule which has the capability of inducing adipose differentiation of adipogenic cells. The adipogenic factors contemplated within the scope of the present invention are not limited to the adipogenic protein or glycoprotein which is purified from liver cells or from serum or fetuin, as described herein, but also to a protein or glycoprotein having adipogenic activity which has been chemically synthesized (by chemical and biochemical techniques) or produced using recombinant DNA technology. The term "adipogenic protein" is intended to encompass a glycoprotein as well.

Furthermore, the liver cell-derived adipogenic protein (HepG2 L-AF) or adipogenic factor, as described herein, may be found in the circulation and appear as a "serum-derived" adipogenic factor or protein. Thus the liver cell-derived, or HepG2 cell-derived, factor or protein may be isolatable from serum as well. Since the cellular source of the serum-derived bovine adipogenic protein (L-AF) or factor described herein is not known, it is possible that this protein or factor is produced and secreted by liver cells, and may thus be isolatable from a liver cell extract or culture supernatant.

In general, the liver cell-derived adipogenic factor or protein of the present invention may be obtained from supernatants of cultured liver cells or tissue, or from extracts, perfusates or other preparations made from liver tissue (freshly obtained or incubated in culture for varying periods of time) or from freshly obtained or cultured normal or tumorous liver cells.

The term "adipogenic" refers to cells or factors which are "fat producing." Thus, an adipogenic cell is a cell which can become an adipocyte (fat cell). An adipogenic factor or protein (or glycoprotein) can induce or stimulate the differentiation of cells which are precursors of adipocytes, such as preadipocytes, to adipocytes. Also intended by the term "adipogenic" factor or protein (or glycoprotein) is a substance which can stimulate proliferation of preadipocytes or adipocytes.

Adipose differentiation can be measured in any of a number of ways which are known to those skilled in the art. A preferred way of measuring adipose differentiation is by the induction of the enzyme G3PDH, as described herein. The assay can be done, without undue experimentation, by one of skill in the art.

The enzyme, glycerol-3-phosphate dehydrogenase (G3PDH), represents a differentiation marker which is suitable for assaying the differentiation-inducing activity of the adipogenic factors or proteins of the present invention and is easy to quantitate. This enzyme is inducible by adipogenic agents. In the presence of an adipogenic factor, the level of G3PDH in an adipogenic cell, such as, for example, in the 1246 cell line, is increased by about 3–10 fold. In the 3T3-L1 cell line the enzyme level is induced as high as 100 fold. Induction of this enzyme is also measurable in primary cultures of epididymal fat pads. The induction of high levels of G3PDH specific enzyme activity is therefore an extremely useful bioassay during purification of an adipogenic factor. A 2-fold increase in the G3PDH activity is considered induction.

In assessing whether a preparation contains an adipogenic factor (protein or glycoprotein) with adipogenic activity "substantially greater" than that of the naturally occurring cells or the serum, one compares the specific adipogenic activity in the preparation with the activity of a liver tissue homogenate or in the conditioned medium of a normal or transformed hepatocyte cell line. "Specific adipogenic activity" refers to the amount of activity per mg (or other weight unit) protein in the preparation.

As alternatives to a purified or recombinant adipogenic protein (or glycoprotein), functional derivatives of the adipogenic protein may be used. By "functional derivative" is meant a "fragment," "variant," "analog," or "chemical derivative" of the adipogenic protein (or glycoprotein), which terms are defined below. A functional derivative retains at least a portion of the function of the adipogenic protein which permits its utility in accordance with the present invention.

A "fragment" of the adipogenic protein refers to any subset of the molecule, that is, a shorter peptide.

A "variant" of the adipogenic protein refers to a molecule substantially similar to either the entire peptide or a fragment thereof. Variant peptides may be conveniently prepared by direct chemical synthesis of the variant peptide, using methods well-known in the art.

Alternatively, amino acid sequence variants of the peptide can be prepared by mutations in the DNA which encodes the synthesized peptide. Such variants include, for example, deletions from, or insertions or substitutions of, residues within the amino acid sequence. Any combination of deletion, insertion, and substitution may also be made to arrive at the final construct, provided that the final construct possesses the desired activity. Obviously, the mutations that will be made in the DNA encoding the variant peptide must not alter the reading frame and preferably will not create complementary regions that could produce secondary mRNA structure (see European Patent Publication No. EP 75,444).

At the genetic level, these variants ordinarily are prepared by site-directed mutagenesis (as exemplified by Adelman et al., *DNA* 2:183 (1983)) of nucleotides in the DNA encoding the peptide molecule, thereby producing DNA encoding the variant, and thereafter expressing the DNA in recombinant cell culture. The variants typically exhibit the same qualitative biological activity as the nonvariant peptide.

An "analog" of the adipogenic protein refers to a non-natural molecule substantially similar to either the entire molecule or a fragment thereof.

A "chemical derivative" of the adipogenic protein contains additional chemical moieties not normally a part of the peptide. Covalent modifications of the peptide are included within the scope of this invention. Such modifications may be introduced into the molecule by reacting targeted amino acid residues of the peptide with an organic derivatizing agent that is capable of reacting with selected side chains or terminal residues.

Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, alpha-bromo-beta-(5-imidozoyl) propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high PKa of the guanidine functional group. Furthermore, these reagents may react with the groups of lysine as well as the arginine epsilon-amino group.

The specific modification of tyrosyl residues Per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl carboxyl side groups (aspartyl or glutamyl) are selectively modified by reaction with carbodiimides (R'—N—C—N—R') such as 1-cyclohexyl-3-(2-morpholinyl-(4-ethyl)carbodiimide or 1-ethyl-3(4-azonia-4, 4-dimethylpentyl)carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Derivatization with bifunctional agents is useful for cross-linking the peptide to a water-insoluble support matrix or to other macromolecular carriers. Commonly used cross-linking agents include, e.g., 1,1-bis(diazoacetyl)-2-phenylethane, glutaraldehyde, N-hydroxysuccinimide esters, for example, esters with 4-azidosalicylic acid, homo-bifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[(p-azidophenyl)] dithiopropioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691, 016; 4,195,128; 4,247,642; 4,229,537; and 4,330,440 are employed for protein immobilization.

Other modifications include hydroxylation of proline and lysine, phosphorylation of hydroxyl groups of seryl or threonyl residues, methylation of the alpha-amino groups of lysine, arginine, and histidine side chains (T. E. Creighton, *Proteins: Structure and Molecule Properties,* W. H. Freeman & Co., San Francisco, pp. 79–86 (1983)), acetylation of the N-terminal amine, and, in some instances, amidation of the C-terminal carboxyl groups.

Such derivatized moieties may improve the solubility, absorption, biological half life, and the like. The moieties may alternatively eliminate or attenuate any undesirable side effect of the protein and the like. Moieties capable of mediating such effects are disclosed, for example, in *Remington's Pharmaceutical Sciences,* 16th ed., Mack Publishing Co., Easton, Pa. (1980)

A "liver cell line" includes hepatocytes derived from a liver or a cell line having hepatocyte functions, including a tumorous hepatocyte line, such as a hepatocarcinoma cell line, as exemplified by HepG2.

"Conditioned medium" refers to any culture medium in which cells have been incubated. A specific example is described herein. Generally, media are chosen that do not have significant deleterious effects on cell viability and the ability of the cell to produce a product which is being purified or assayed in a bioassay.

For use as an antigen for induction of antibodies, a fraction of the HepG2 derived human adipogenic factor, or a serum-derived adipogenic factor, preferably a purified adipogenic protein or glycoprotein, is obtained as described herein and used to immunize an animal. In a preferred embodiment, a mouse is immunized with this antigen. In a more preferred embodiment, the mouse is of the inbred strain, Balb/c. The term "antibody" refers both to monoclonal antibodies (mAbs) which are a substantially homogeneous population and to polyclonal antibodies which are heterogeneous populations. Polyclonal antibodies are derived from the sera of animals immunized with the above antigen stein, *Nature* 256:495–497 (1975) and U.S. Pat. No. 4,376,110. Such antibodies may be of any immunoglobulin class including IgG, IgM, IgE, IgA, IgD and any subclass thereof.

Hybridoma supernatants are screened for the presence of antibody specific for the adipogenic protein by any of a number of immunoassays, including dot blots and standard enzyme immunoassays (EIA or ELISA), which are well-known in the art. Once a supernatant has been identified as having antibodies, it may be further screened by Western blotting to identify the size of the antigen to which the antibody binds. One of skill in the art will know how to prepare and screen such hybridomas without undue experimentation.

The term "antibody" is also meant to include both intact molecules as well as fragments thereof, such as, for example, Fab and F(ab')$_2$, which are capable of binding the antigen. Fab and F(ab')$_2$ fragments lack the Fc fragment of intact antibody, clear more rapidly from the circulation, and may have less non-specific tissue binding than an intact antibody (Wahl et al., *J. Nucl. Med.* 24:316–325 (1983)).

It will be appreciated that Fab and F(ab')$_2$ and other used for the detection and quantitation of adipogenic proteins according in the same manner as an intact antibody. Such fragments are typically produced by proteolytic cleavage, using enzymes such as papain (to produce Fab fragments) or pepsin (to produce F(ab')$_2$ fragments).

Polyclonal or monoclonal antibodies can be used in an immunoaffinity column to purify an adipogenic protein by a one step procedure, using methods known in the art.

The antibodies of the invention are useful for detecting and quantitate the adipogenic proteins in an immunoassay, such as, for example, radioimmunoassay (RIA) or enzyme immunoassay (EIA). Such assays are well-known in the art, and one of skill will readily know how to carry out such assays using the antibodies and adipogenic proteins of the present invention.

Such immunoassays are useful for detecting and quantitating an adipogenic protein in the serum or other biological fluid, or in a tissue sample or tissue extract, from a normal or obese subject. In a preferred embodiment, the concentration of one or more of the adipogenic proteins of this invention is measured in a tissue extract or biological fluid of a subject as a means for determining the susceptibility or the propensity of the subject for obesity.

The susceptibility of a subject to obesity is said to be proportional to the level of the adipogenic protein. The term "proportional" as used herein is not intended to be limited to a linear or constant relationship between the level of the adipogenic protein and the susceptibility to obesity. The nature of the relationship between factor level and susceptibility or propensity to obesity may be highly complex. For example, the doubling of the concentration of an adipogenic protein is not necessarily indicative of a doubling in the susceptibility to obesity. The term "proportional" as used herein is intended to indicate that an increased level of factor is related to an increased propensity to obesity at ranges of concentration of the factor that can be readily determined by one of skill in the art.

Another embodiment of the invention is evaluating the efficacy of anti-obesity drug or agent by measuring the ability of the drug or agent being evaluated to inhibit the production of one or more of the adipogenic proteins of this invention by a cell or cell line capable of producing such factors. The antibodies of the present invention are useful in the method for evaluating anti-obesity drugs in that they can be employed to determine the amount of the adipogenic protein in one of the above-mentioned immunoassays. Alternatively, the amount of adipogenic protein produced is measured by bioassay, as described herein. The bioassay and immunoassay can be used in combination for a more precise assessment of the factor or factors present.

One embodiment of the present invention is directed to polynucleotide molecules, particularly DNA, encoding the adipogenic proteins. Another embodiment is directed to the preparation of the adipogenic proteins using recombinant DNA techniques. Also intended are vectors comprising the DNA, and host cells transformed or transfected with the DNA encoding an adipogenic protein.

The DNA encoding the polypeptide portion of the adipogenic proteins of the present invention is either synthesized chemically, prepared as genomic DNA, or prepared as cDNA from cellular mRNA. DNA sequences encoding the adipogenic protein or a portion or a variant thereof are inserted into an appropriate vector, such as a plasmid or virus, and introduced into an appropriate host cell, either prokaryotic or eukaryotic. Such techniques are set forth, for example, in Sambrook et al. (*Molecular Cloning: A Laboratory Manual,* Second edition, Cold Spring Harbor Laboratory Press, 1989), which is hereby incorporated by reference.

Based on the amino acid sequence of the adipogenic protein, oligonucleotide probes can be prepared and used to isolated DNA (genomic or cDNA) encoding the protein. Techniques for synthesizing such oligonucleotides are disclosed by, for example, Wu, R., et al., *Prog. Nucl. Acid. Res. Molec. Biol.* 21:101–141 (1978). Procedures for constructing recombinant molecules in accordance with the above-described method are disclosed by Sambrook, J. et al. (supra). Molecules are fragmented as with cyanogen bromide, or with proteases such as papain, chymotrypsin, trypsin, etc. (Oike, Y., et al., *J. Biol. Chem.* 257:9751–9758 (1982); Liu, C., et al., *Int. J. Pept. Protein Res.* 21:209–215 (1983)). Because the genetic code is degenerate, more than one codon may be used to encode a particular amino acid (Watson, J. D., In: *Molecular Biology of the Gene,* 4th Ed., Benjamin/Cummings Publishing Co. Inc., Menlo Park, Calif. (1987)). Using the genetic code, one or more different oligonucleotides can be identified, each of which would be capable of encoding a portion of the adipogenic protein. The probability that a particular oligonucleotide will, in fact, constitute the actual adipogenic protein-encoding sequence can be estimated by considering abnormal base pairing relationships and the frequency with which a particular codon is actually used (to encode a particular amino acid) in eukaryotic cells. Such "codon usage rules" are disclosed by Lathe, R., et al., *J. Molec. Biol.* 183:1–12 (1985). Using the "codon usage rules" of Lathe, a single oligonucleotide, or a set of oligonucleotides, that contains a theoretical "most probable" nucleotide sequence capable of encoding the adipogenic protein sequences is identified.

Although occasionally an amino acid sequences may be encoded by only a single oligonucleotide, frequently the amino acid sequence may be encoded by any of a set of similar oligonucleotides. Importantly, whereas all of the members of this set contain oligonucleotides which are capable of encoding the adipogenic protein fragment and, thus, potentially contain the same oligonucleotide sequence as the gene which encodes the peptide fragment, only one member of the set contains the nucleotide sequence that is identical to the nucleotide sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide.

The oligonucleotide, or set of oligonucleotides, containing the theoretical "most probable" sequence capable of encoding the adipogenic peptide is used to identify the sequence of a complementary oligonucleotide or set of oligonucleotides which is capable of hybridizing to the "most probable" sequence, or set of sequences. An oligonucleotide containing such a complementary sequence can be employed as a probe to identify and isolate the adipogenic protein gene (Sambrook, J. et al., supra).

A suitable oligonucleotide, or set of oligonucleotides, which is capable of encoding a fragment of the adipogenic protein gene (or which is complementary to such an oligonucleotide, or set of oligonucleotides) is identified (using the above-described procedure), synthesized, and hybridized by means well known in the art, against a DNA or, more preferably, a cDNA preparation derived from cells which are capable of expressing the adipogenic protein gene, such as, for example, HepG2. Single stranded oligonucleotide molecules complementary to the "most probable" adipogenic protein peptide encoding sequences can be synthesized using procedures which are well known to those of ordinary skill in the art (Belagaje, R., et al., *J. Biol. Chem.* 254:5765–5780 (1979); Maniatis, T., et al., In: *Molecular Mechanisms in the Control of Gene Expression,* Nierlich, D. P., et al., Eds., Acad. Press, New York (1976); Wu, R., et al., *Prog. Nucl. Acid Res. Molec. Biol.* 21:101–141 (1978); Khorana, R. G., *Science* 203:614–625 (1979)). Additionally, DNA synthesis may be achieved through the use of automated synthesizers. Techniques of nucleic acid hybridization are disclosed by Sambrook, J. et al. (supra) and by Haymes, B. D., et al. (In: *Nucleic Acid Hybridization, A Practical Approach,* IRL Press, Washington, D.C. (1985), which references are herein incorporated by reference. Techniques such as, or similar to, those described above have successfully enabled the cloning of genes for human aldehyde dehydrogenases (Hsu, L. C., et al., *Proc. Natl. Acad. Sci. USA* 82:3771–3775 (1985), fibronectin (Suzuki, S., et al., *Eur. Mol. Biol. Organ. J.* 4:2519–2524 (1985), the human estrogen receptor gene (Walter, P., et al., *Proc. Natl. Acad. Sci. USA* 82:7889–7893 (1985)), tissue-type plasminogen activator (Pennica, D., et al., *Nature* 301:214–221 (1983)) and human term placental alkaline phosphatase complementary DNA (Kam, W., et al., *Proc. Natl. Acad. Sci. USA* 82:8715–8719 (1985).

In an alternative way of cloning the adipogenic protein gene, a library of expression vectors is prepared by cloning DNA or, more preferably, cDNA (from a cell capable of expressing adipogenic protein, such as HepG2) into an expression vector. The library is then screened for members capable of expressing a protein which binds to anti-adipogenic protein antibody, and which has a nucleotide sequence that is capable of encoding polypeptides that have the same amino acid sequence as adipogenic protein, or fragments thereof. In this embodiment, DNA, or more preferably cDNA, is extracted and purified from a cell which is capable of expressing adipogenic protein antigen. The purified cDNA is fragmentized (by shearing, endonuclease digestion, etc.) to produce a pool of DNA or cDNA fragments. DNA or cDNA fragments from this pool are then cloned into an expression vector in order to produce a genomic library of expression vectors whose members each contain a unique cloned DNA or cDNA fragment.

An "expression vector" is a vector which (due to the presence of appropriate transcriptional and/or translational control sequences) is capable of expressing a DNA (or cDNA) molecule which has been cloned into the vector and of thereby producing a polypeptide or protein. Expression of the cloned sequences occurs when the expression vector is introduced into an appropriate host cell. If a prokaryotic expression vector is employed, then the appropriate host cell would be any prokaryotic cell capable of expressing the cloned sequences. Similarly, if a eukaryotic expression vector is employed, then the appropriate host cell would be any eukaryotic cell capable of expressing the cloned sequences. Importantly, since eukaryotic DNA may contain intervening sequences, and since such sequences cannot be correctly processed in prokaryotic cells, it is preferable to employ cDNA from a cell which is capable of expressing adipogenic protein in order to produce a prokaryotic genomic expression vector library. Procedures for preparing cDNA and for producing a genomic library are disclosed by Sambrook, J. et al. (supra).

Nucleic acid detection assays can be predicated on any characteristic of the nucleic acid molecule, such as its size, sequence, susceptibility to digestion by restriction endonucleases, etc. The sensitivity of such assays may be increased by altering the manner in which detection is reported or signaled to the observer. Thus, for example, assay sensitivity can be increased through the use of detectably labeled reagents. A wide variety of such labels have been used for this purpose. Kourilsky et al. (U.S. Pat. No. 4,581,333) describe the use of enzyme labels to increase sensitivity in a detection assay. Radioisotopic labels are disclosed by Falkow et al. (U.S. Pat. No. 4,358,535), and by Berninger (U.S. Pat. No. 4,446,237). Fluorescent labels (Albarella et al., EP 144914), chemical labels (Sheldon III et al., U.S. Pat. No. 4,582,789; Albarella et al., U.S. Pat. No. 4,563,417), modified bases (Miyoshi et al., EP 119448), etc. have also been used in an effort to improve the efficiency with which detection can be observed.

One method for overcoming the sensitivity limitation of nucleic acid concentration is to selectively amplify the nucleic acid whose detection is desired prior to performing the assay.

Recombinant DNA methodologies capable of amplifying purified nucleic acid fragments have long been recognized. Typically, such methodologies involve the introduction of the nucleic acid fragment into a DNA or RNA vector, the clonal amplification of the vector, and the recovery of the amplified nucleic acid fragment. Examples of such methodologies are provided by Cohen et al. (U.S. Pat. No. 4,237,224), Maniatis, T., et al., etc.

Recently, an in vitro, enzymatic method has been described which is capable of increasing the concentration of such desired nucleic acid molecules. This method has been referred to as the "polymerase chain reaction or "PCR" (Mullis, K. et al., *Cold Spring Harbor Symp. Quant. Biol.* 51:263–273 (1986); Erlich H. et al., EP 50,424; EP 84,796, EP 258,017, EP 237,362; Mullis, K., EP 201,184; Mullis K. et al., U.S. Pat. No. 4,683,202; Erlich, H., U.S. Pat. No. 4,582,788; and Saiki, R. et al., U.S. Pat. No. 4,683,194).

The polymerase chain reaction provides a method for selectively increasing the concentration of a particular nucleic acid sequence even when that sequence has not been previously purified and is present only in a single copy in a particular sample. The method can be used to amplify either single- or double-stranded DNA. The essence of the method involves the use of two oligonucleotide probes to serve as primers for the template-dependent, polymerase mediated replication of a desired nucleic acid molecule.

The precise nature of the two oligonucleotide probes of the PCR method is critical to the success of the method. As is well known, a molecule of DNA or RNA possesses directionality, which is conferred through the 5'-3' linkage of the phosphate groups of the molecule. Sequences of DNA or RNA are linked together through the formation of a phosphodiester bond between the terminal 5' phosphate group of one sequence and the terminal 3' hydroxyl group of a second sequence. Polymerase dependent amplification of a nucleic acid molecule proceeds by the addition of a 5' nucleotide triphosphate to the 3' hydroxyl end of a nucleic acid molecule. Thus, the action of a polymerase extends the 3' end of a nucleic acid molecule. These inherent properties are exploited in the selection of the oligonucleotide probes of the PCR. The oligonucleotide sequences of the probes of the PCR method are selected such that they contain sequences identical to, or complementary to, sequences which flank the particular nucleic acid sequence whose amplification is desired. More specifically, the oligonucleotide sequences of the "first" probe is selected such that it is capable of hybridizing to an oligonucleotide sequence located 3' to the desired sequence, whereas the oligonucleotide sequence of the "second" probe is selected such that it contains an oligonucleotide sequence identical to one present 5' to the desired region. Both probes possess 3' hydroxy groups, and therefore can serve as primers for nucleic acid synthesis.

In the polymerase chain reaction, the reaction conditions are cycled between those conducive to hybridization and nucleic acid polymerization, and those which result in the denaturation of duplex molecules. In the first step of the reaction, the nucleic acids of the sample are transiently heated, and then cooled, in order to denature any double-stranded molecules which may be present. The "first" and "second" probes are then added to the sample at a concentration which greatly exceeds that of the desired nucleic acid molecule. When the sample is incubated under conditions conducive to hybridization and polymerization, the "first" probe will hybridize to the nucleic acid molecule of the sample at a position 3' to the sequence to be amplified. If the nucleic acid molecule of the sample was initially double-stranded, the "second" probe will hybridize to the complementary strand of the nucleic acid molecule at a position 3' to the sequence which is the complement of the sequence whose amplification is desired. Upon addition of a polymerase, the 31 ends of the "first" and (if the nucleic acid molecule was double-stranded) "second" probes will be extended. The extension of the "first" probe will result in the synthesis of an oligonucleotide having the exact sequence of the desired nucleic acid. Extension of the "second" probe will result in the synthesis of an oligonucleotide having the exact sequence of the complement of the desired nucleic acid.

The PCR reaction is capable of exponential amplification of specific nucleic acid sequences because the extension product of the "first" probe, of necessity, contains a sequence which is complementary to a sequence of the "second" probe, and thus can serve as a template for the production of an extension product of the "second" probe. Similarly, the extension product of the "second" probe, of necessity, contains a sequence which is complementary to a sequence of the "first" probe, and thus can serve as a template for the production of an extension product of the "first" probe. Thus, by permitting cycles of polymerization, and denaturation, a geometric increase in the concentration of the desired nucleic acid molecule can be achieved. Reviews of the polymerase chain reaction are provided by Mullis, K. B. (*Cold Spring Harbor Symp. Quant. Biol.* 51:263–273 (1986); Saiki, R. K., et al. (*Bio/Technology* 3:1008–1012 (1985)); and Mullis, K. B., et al. (*Met. Enzymol.* 155:335–350 (1987)).

The above-described recombinant molecules can be produced through any of a variety of means, such as, for example, DNA or RNA synthesis, or more preferably, by application of recombinant DNA techniques. Techniques for synthesizing such molecules are disclosed by, for example, Wu, R., et al. (*Prog. Nucl. Acid. Res. Molec. Biol.* 21:101–141 (1978)). Procedures for constructing recombinant molecules in accordance with the above-described method are disclosed Sambrook et al. (supra) The 3' terminus of the above-described recombinant molecule is preferably treated to render it unsuitable for polymerization. Such treatment may be accomplished by blocking the terminus by chemical means, or by modifying the terminal bases such that they sterically interfere with polymerase action. In a preferred embodiment, such treatment is accomplished by immobilizing the 3' terminus, such as by coupling it to a solid support (such as, for example, glass, plastic, latex, etc.). The support may be of any form (i.e. a sheet, rod, sphere, ovoid, etc. Procedures for such immobilization are well known to those of ordinary skill. In the most preferred embodiment, the 3' end of the recombinant molecule is covalently bound to the solid support. A spacer region may be used to extend the probe outward from the solid support as long as (1) it will not sterically hinder any function or characteristic of the recombinant molecule, and (2) the sequence of the spacer region does not participate in the hybridization or polymerization reactions of the assay. It is typically desirable to immobilize several, and preferably, a large number of such recombinant molecule to the support.

For expression of the DNA encoding the adipogenic protein of the present invention, a genetic construct is produced that possesses the necessary control elements to permit appropriate transcription and translation of the nucleic acid sequence. A promoter is a double-stranded DNA or RNA molecule which is capable of binding RNA polymerase and promoting the transcription of an "operably linked" nucleic acid sequence. As used herein, a "promoter sequence" is the sequence of the promoter which is found on that strand of the DNA or RNA which is transcribed by the RNA polymerase. A "promoter sequence complement" is a nucleic acid molecule whose sequence is the complement of a "promoter sequence." Hence, upon extension of a primer DNA or RNA adjacent to a single-stranded "promoter sequence complement" or, of a "promoter sequence," a double-stranded molecule is created which will contain a functional promoter, if that extension proceeds a nucleic acid molecule which is operably linked to that strand of the double-stranded molecule which contains the "promoter sequence" (and not that strand of the molecule which contains the "promoter sequence complement").

Certain RNA polymerases exhibit a high specificity for such promoters. The RNA polymerases of the bacteriophages T7, T3, and SP-6 are especially well characterized, and exhibit high promoter specificity. The promoter sequences which are specific for each of these RNA polymerases also direct the polymerase to utilize (i.e. transcribe) only one strand of the two strands of a duplex DNA template. The selection of which strand is transcribed is determined by the orientation of the promoter sequence. This selection determines the direction of transcription since RNA is only polymerized enzymatically by the addition of a nucleotide 5' phosphate to a 3' hydroxyl terminus.

Two sequences of a nucleic acid molecule are said to be "operably linked" when they are linked to each other in a manner which either permits both sequences to be transcribed onto the same RNA transcript, or permits an RNA transcript, begun in one sequence to be extended into the second sequence. Thus, two sequences, such as a promoter sequence and any other "second" sequence of DNA or RNA are operably linked if transcription commencing in the promoter sequence will produce an RNA transcript of the operably linked second sequence. In order to be "operably linked" it is not necessary that two sequences be immediately adjacent to one another.

Thus, as indicated above, in order to function as a promoter, a promoter sequence must be present as a double-stranded molecule. The promoter sequences of the present invention may be either prokaryotic, eukaryotic or viral. Suitable promoters are repressible, or, more preferably, constitutive. Examples of suitable prokaryotic promoters include promoters capable of recognizing the T4 (Malik, S. et al., *J. Biol. Chem.* 263:1174–1181 (1984); Rosenberg, A. H. et al., *Gene* 59:191–200 (1987); Shinedling, S. et al., *J. Molec. Biol.* 195:471–480 (1987); Hu, M. et al., *Gene* 42:21–30 (1986), T3, Sp6, and T7 (Chamberlin, M. et al., *Nature* 228:227–231 (1970); Bailey, J. N. et al., *Proc. Natl. Acad. Sci. (U.S.A.)* 80:2814–2818 (1983); Davanloo, P. et al., *Proc. Natl. Acad. Sci. (U.S.A.)* 81:2035–2039 (1984) polymerases; the $P_R$ and $P_L$ promoters of bacteriophage 1 (*The Bacteriophage Lambda,* Hershey, A. D., Ed., Cold Spring Harbor Press, Cold Spring Harbor, N.Y. (1973); *Lambda II,* Hendrix, R. W., Ed., Cold Spring Harbor Press, Cold Spring Harbor, N.Y. (1980); the trp, recA, heat shock, and lacZ promoters of *E. coli;* the a-amylase (Ulmanen, I., et al.,*J. Bacteriol.* 162:176–182 (1985) and the s-28-specific promoters of *B. subtilis* (Gilman, M. Z., et al., *Gene* 32:11–20 (1984)); the promoters of the bacteriophages of Bacillus (Gryczan, T. J., In: *The Molecular Biology of the Bacilli,* Academic Press, Inc., New York (1982)); Streptomyces promoters (Ward, J. M., et al., *Mol. Gen. Genet.* 203:468–478 (1986)); the int promoter of bacteriophage l; the bla promoter of the b-lactamase gene of pBR322, and the CAT promoter of the chloramphenicol acetyl transferase gene of pPR325, etc. Prokaryotic promoters are reviewed by Glick, B. R., (*J. Ind. Microbiol.* 1:277–282 (1987); Cenatiempo, Y. (*Biochimie* 68:505–516 (1986); Watson, J. D. et al. (supra); and Gottesman, S. (*Ann. Rev. Genet.* 18:415–442 (1984)). Preferred eukaryotic promoters include the promoter of the mouse metallothionein I gene (Hamer, D., et al., *J. Mol. Appl. Gen.* 1:273–288 (1982)); the TK promoter of Herpes virus (McKnight, S., *Cell* 31:355–365 (1982)); the SV40 early promoter (Benoist, C., et al., *Nature* (London) 290:304–310 (1981)); and the yeast gal4 gene promoter (Johnston, S. A., et al., *Proc. Natl. Acad. Sci. (USA)* 79:6971–6975 (1982); Silver, P. A., et al.,*Proc. Natl. Acad. Sci. (USA)* 81:5951–5955 (1984).

All of the above listed references are incorporated by reference herein.

Strong promoters are the most preferred promoters of the present invention. Examples of such preferred promoters are those which recognize the T3, SP6 and T7 polymerase promoters; the $P_L$ promoter of bacteriophage lambda; the recA promoter and the promoter of the mouse metallothionein I gene. The most preferred promoter is one which is capable of recognizing the T7 polymerase promoter. The sequences of such polymerase recognition sequences are disclosed by Watson, J. D. et al. (supra).

For purification and characterization of the proteins, sodium dodecyl sulfate polyacrylamide gel electrophoresis (SDS-PAGE) is performed in general according to the method of Laemmli (1974) using 7.5% acrylamide gels with a constant ratio of 2.6% bisacrylamide/total acrylamide concentration. Protein samples are denatured at 100° C. for 10 min in 20 mM Tris containing 3.3% glycerol, and bromophenol blue tracking dye with or without proteins with 0.05% R250 Coomassie brilliant blue in 25% isopropanol for 2 h, and destained for 24 h in 20% methanol-7% acetic acid. As molecular weight markers, myosin (200 kDa), beta-galactosidase (116 kDa), phosphorylase B (97 kDa), BSA (66 kDa), and egg albumin (43 kDa) are used. Known modifications and variations of the described method are also contemplated within the scope of this invention.

The preferred animal subject of the present invention is mammal. By the term "mammal" is intended an individual belonging to the class Mammalia. The invention is particularly useful in the treatment of human subjects, although it is intended for veterinary uses as well.

The following examples are intended to be illustrative, but not to limit, the invention.

EXAMPLE I

GENERAL METHODS FOR STUDY OF ADIPOGENIC FACTORS

Conditions for the culture of 1246 cells useful for the bioassay of adipogenic factors are modifications of methods described previously (Serrero and Khoo (1982), *Anal. Biochem.* 120, 351–359; G. Serrero, (1985), *In Vitro Cell. Dev. Biol.* 21, 537–540), and are hereby incorporated by reference.

1246 cells, derived from C3H mouse teratoma, were cultivated in tissue culture plasticware (Costar, Cambridge, Mass.) in Dulbecco's modified Eagle's medium/Ham's F12 nutrient mixture (1:1 mixture)(Gibco, Grand Island, N.Y.) (referred to as DME/F12) supplemented with 1.2 g/l sodium bicarbonate (Sigma, St. Louis, Mo.), 15 mM HEPES pH 7.4 (Research Organics, Cleveland, Ohio) and 10% fetal calf serum (FCS)(Hyclone, Logan, Utah) in humidified atmosphere of 95% air-50% $CO_2$ at 37° C.

Adipose differentiation assay

On day 0, subconfluent 1246 cells were plated at a density of $1.5 \times 10^4$ cells per well (having a surface area of 4.5 cm$^2$) in 12-well cluster plates (Costar) in DM/F12 medium supplemented with 2% FCS. At day 1, the medium was replaced by DME/F12 supplemented with insulin (10 μg/ml) (Sigma, St. Louis, Mo.), transferrin (10 μg/ml) (Sigma), and fibroblast growth factor (5 ng/ml) (Collaborative Research, Waltham Mass.). Cells were exposed to dexamethasone ($2 \times 10^{-7}$M) (Sigma), isobutylmethylxanthine ($2 \times 10^{-4}$M) (Aldrich Chemical Co., Milwaukee, Wis.), and indomethacin ($3 \times 10^{-5}$M) (Sigma) from day 4 to day 6. Cells were further incubated in DME/F12 containing insulin and transferrin, and were harvested at day 11. Adipose differentiation was examined by measurement of G3PDH specific activity as described above. Fetuin (Sigma) and/or partially purified fractions (from fetuin or HepG2-CM) were added at day 1, day 4 and day 6. When cells were harvested, duplicate wells were pooled and used for the assay. Control plates had cells cultivated in defined medium alone, without fetuin.

SEPHACRYL fractionation

SEPHACRYL S-300 (Pharmacia, Piscataway, N.J.) column (2.5 cm×95 cm) was equilibrated and run in 20 mM phosphate buffer-0.1M NaCl pH 7.0 at a flow rate of 20 ml/hr at 4° C. Thyroglobulin (669 kDa), ferritin (445 kDa), catalase (232 kDa), and bovine serum albumin (BSA) (69 kDa) contained in the gel filtration calibration kit (Pharmacia) were used as molecular weight markers.

Heparin-SEPHAROSE chromatography of the 30–50% ammonium sulfate fraction of HePG2-derived human adipogenic factor Preparation This fraction (195 ml) was diluted with ultrapure water to adjust the conductivity to 15 mS/cm (15 mmho) and applied to a heparin-SEPHAROSE CL-6B column (4.2×20 cm) using 20 mM sodium phosphate buffer, pH 7.0. The column was washed with the same buffer and subsequently with the same buffer containing 0.35M NaCl at flow rate of 120 ml/h. Adipogenic activity was eluted with the same buffer containing 1M NaCl at flow rate of 50 ml/h. The activity was separated into two fractions, denoted fraction I and II (see FIG. 1).

Biochemical characterization of adipogenic factors

Partially purified fractions from fetuin and from HepG2 CM were used for biochemical characterization experiments. Acid sensitivity or alkali sensitivity was tested by incubating samples at pH 2.5 or pH 11.0 for 24 h at 4° C. Heat stability was examined by heating a factor in 20 mM phosphate buffer, pH 7.0 for 10 min. Sensitivity to disulfide-reducing agent was tested by incubating samples with 0.2M 2-mercaptoethanol at room temperature for 6 h. All the treated samples were dialyzed against 20 mM phosphate buffer (pH 7.0) before being assayed. Protease sensitivity was examined by incubating samples with immobilized pronase conjugated to agarose beads (*Streptomyces griseus*, Sigma) at 37° C. for 6 h. Pronase was removed by centrifugation before use.

EXAMPLE II

INITIAL PURIFICATION AND CHARACTERIZATION OF HUMAN ADIPOGENIC FACTOR FROM HEPG2 CELLS

The starting material for large scale purification of the human adipogenic factor was the culture medium conditioned by the HepG2 cells. The HepG2 cell line is available from American Type Culture collection (ATCC HB 8065). For the isolation of this factor, see Aden, D. P. et al. (1979) Nature 282 615. HepG2 cells were cultivated in defined medium, RITC-807 medium+10% FBS. RITC-807 medium is described in Kan, M. et al., (1982) *J. Cell Physiol.* 111:155–162. At confluence, they were cultivated RITC-807 medium. In these conditions, the cells secreted several proteins in the culture medium including the adipogenic factor.

Conditioned medium from HepG2 cells was concentrated 25-fold by ultrafiltration with a 10,000 molecular weight cut-off Filtron membrane system. Ammonium sulfate precipitation was carried out as using standard procedures which are well-known in the art. The protein factor precipitated by 30–50% (w/v) ammonium sulfate was resuspended in phosphate buffer (20 mM, pH 7.0) and diluted. The diluted fraction was chromatographed on a heparin-sepharose column equilibrated in 20 mM sodium phosphate buffer pH 7.0. The active fraction was eluted with a gradient of NaCl between 0.35M–1M NaCl (see FIG. 1). Eluted fractions were loaded onto a concanavalin A SEPHAROSE column equilibrated with 20 mM phosphate buffer pH 7.0 containing 0.5M NaCl. The active fraction was eluted with 0.5M (alpha) methylmannoside in 20 mM phosphate buffer pH 7.0. The active fraction was then loaded on a SEPHACRYL S-300 column or on a SEPHAROSE CL-6B column equilibrated in 20 mM phosphate buffer pH 7.0 containing 0.1M NaCl. The active fraction was eluted with an apparent molecular weight of 150 kDa to 230 kDa, as detected by SDS-PAGE analysis. (Upon further purification, these molecular weights were later determined to be about 150 and 170 kDa; see below).

TABLE 1

SPECIFIC ACTIVITY OF HUMAN ADIPOGENIC FACTOR DURING PURIFICATION FROM HEPG2 CONDITIONED MEDIUM.

| Source or Conditions | Protein Recovery (%) | Specific Activity* |
|---|---|---|
| Conditioned medium | 100 | 1 |
| Ammonium sulfate ppt. (30–50%) w/v | 35 | 2.5 |
| Heparin SEPHAROSE | 2 | 25 |
| Concanayalin SEPHAROSE | 1 | 50 |
| SEPHAROSE CL6B (or SEPHACRYL S-300) | 0.03 | 625 |

*Measured by the induction of glycerol-3-phosphate dehydrogenase activity using the bioassay described herein.

For the HepG2 factor that underwent the above purification procedure, only three major bands were detectable after PAGE (without SDS) after silver staining of the gel. The adipogenic factor represented at least 30% of the total protein in the fraction.

Characterization of human adipogenic factor

The human adipogenic factor, isolated as described above, was analyzed by SDS-PAGE. A major band appeared to have a molecular weight of 230 kDa and two minor bands were of lower molecular weight. Additional experiments revealed that the higher molecular weight adipogenic activity was destroyed by incubation with pronase (indicating it is a protein), by heat treatment (100° C., 5 minutes) and by incubation at pH 2.5 for 24 hr at 4° C. and by treatment with 0.2M 2-mercaptoethanol at room temperature (about 25° C.) for 6 hours, indicating the existence of disulfide bridges which are important for the maintenance of its biological activity. About 60% of the adipogenic activity remained after exposure to pH 11.0 for 24 hours at 4° C.

EXAMPLE III

PURIFICATION AND CHARACTERIZATION OF A LOW MOLECULAR WEIGHT ADIPOGENIC FACTOR (HePG2 L-AF) PRODUCED BY HepG2 CELLS

Purification of the adipogenic protein produced by hepatocytes and HepG2 cells was performed using conditioned medium from HepG2 cells (HepG2-CM) as starting material. The larger molecular weight form of the Adipogenic protein was further purified according to the following scheme:

1. HepG2 conditioned medium
2. Concentrated 25- to 40-fold by ultrafiltration; molecular weight cut off at 10,000 Da.
3. Ammonium sulfate precipitation, 30%–50%
4. Pellet resuspended in water, conductivity adjusted to conductivity of 20 mM phosphate buffer pH 7.0
5. Heparin-SEPHAROSE chromatography, pH 7.0 20 mM Na phosphate buffer
   a. Wash with equilibrium buffer
   b. Wash with 20 mM Na phosphate buffer, pH 7.0, NaCl 0.3M
   c. Elute with 20 mM Na phosphate buffer pH 7.0, NaCl 1M
6. SEPHAROSE CL-6B chromatography equilibrated in 20 mM Na phosphate pH 7.0, 0.5M NaCl
7. MONO Q SEPHAROSE chromatography equilibrated in 20 mM Na phosphate, pH 7.0 ; elute with NaCl gradient 0 to 0.5M NaCl

TABLE 2

Purification of Adipogenic protein from HepG2 CM According to the above Purification Scheme

| Procedure | Protein Recovery (%) | Activity Recovery (%) | Purification Factor (Fold) |
|---|---|---|---|
| HepG2 (HepG2 CM) conditioned medium | 100 | 100 | 1.0 |
| Ammonium sulfate ppt (30–50%) | 32 | 109 | 3.4 |
| Heparin SEPHAROSE (0.35–1.0 M NaCl) | 1.4 | 47.6 | 34 |
| SEPHAROSE CL6B | 0.06 | 24.5 | 408 |
| MONO Q (0.35–0.38 M NaCl) | 0.005 | 8.2 | 1,633 |

Adipogenic activity is expressed as G3PDH specific activity which is calculated by subtracting activity in control culture (no addition) from the activity obtained in the presence of samples to assay.

2. Characterization of Human Adipogenic Factor

Figure 2:
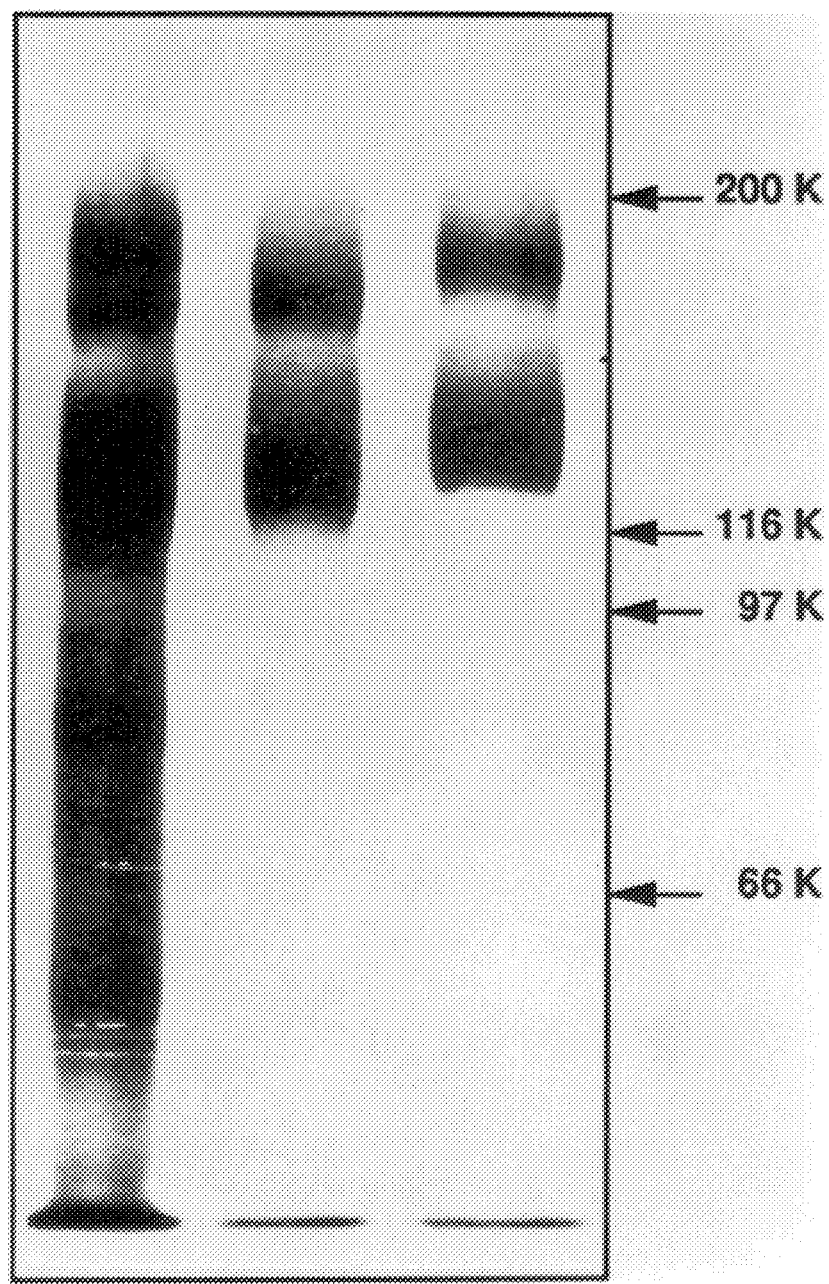
FIG. 2 is a gel pattern showing the results of polyacrylamide gel electrophoresis of adipogenic factor from MONO Q SEPHAROSE chromatography after purification scheme described in Example III. Lane 1: Parent sample (active fraction eluted from SEPHAROSE CL6B); lanes 2 and 3: Active fractions eluted from MONO Q SEPHAROSE columns.

The human adipogenic factor, isolated using the methods as described above, was analyzed by SDS-PAGE. The analysis revealed two bands with a molecular weight of 170 kDa and 150 kDa (FIG. 2).

Biochemical characterization of the purified adipogenic fraction from HepG2 CM indicated that the of the frecular weight of the fraction was due to aggregation of the protein either to itself or to the large molecular weight protein. The existence of these protein-protein interactions most probably resulted in limited progress in purification and in poor yields of purification of the adipogenic factor (only 8% after three steps of purification). This observation prompted the present inventors to develop a purification procedure under conditions wherein protein-protein interaction would be minimized.

Figure 3A:
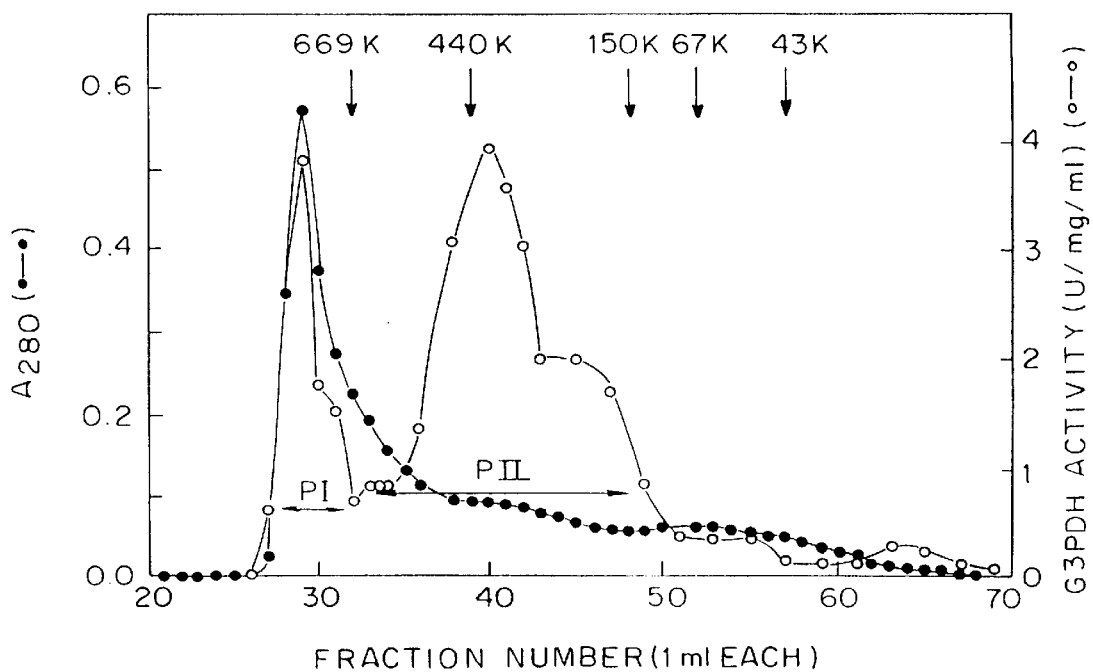
FIG. 3 shows the results of molecular-sieve chromatography of heparin SEPHAROSE fraction I (see FIG. 1) and its dissociated protein on a SEPHACRYL S-300 column. PANEL A: 1.1 ml of a concentrated Fraction I (starting at 9.7 mg/9 ml) was applied to a SEPHACRYL S-300 column (1.6×50 cm) in 20 mM sodium phosphate buffer, pH 7.0 containing 0.15M NaCl. PANEL B: an aliquot of concentrated Fraction I (0.36 ml) was mixed with 0.04 ml of 10% n-octyl, β-D-glucopyranoside (OG) in 20 mM sodium phosphate buffer, pH 7.0 and incubated at 0° C. for 15 min. After incubation, the mixture was sonicated for 2 min under cooling conditions and applied to a column as in PANEL A in 20 mM sodium phosphate buffer, pH 7.0 containing 0.4% 3-[(3-cholamidopropyl)-dimethylammonio]-1-propane sulfonate (CHAPS) and 0.5M NaCl. Arrows indicate the elution position of thyroglobulin (669 kDa), ferritin (440 kDa), IgG (150 kDa), bovine serum albumin (67 kDa) and ovalbumin (43 kDa), respectively.
Figure 3B:
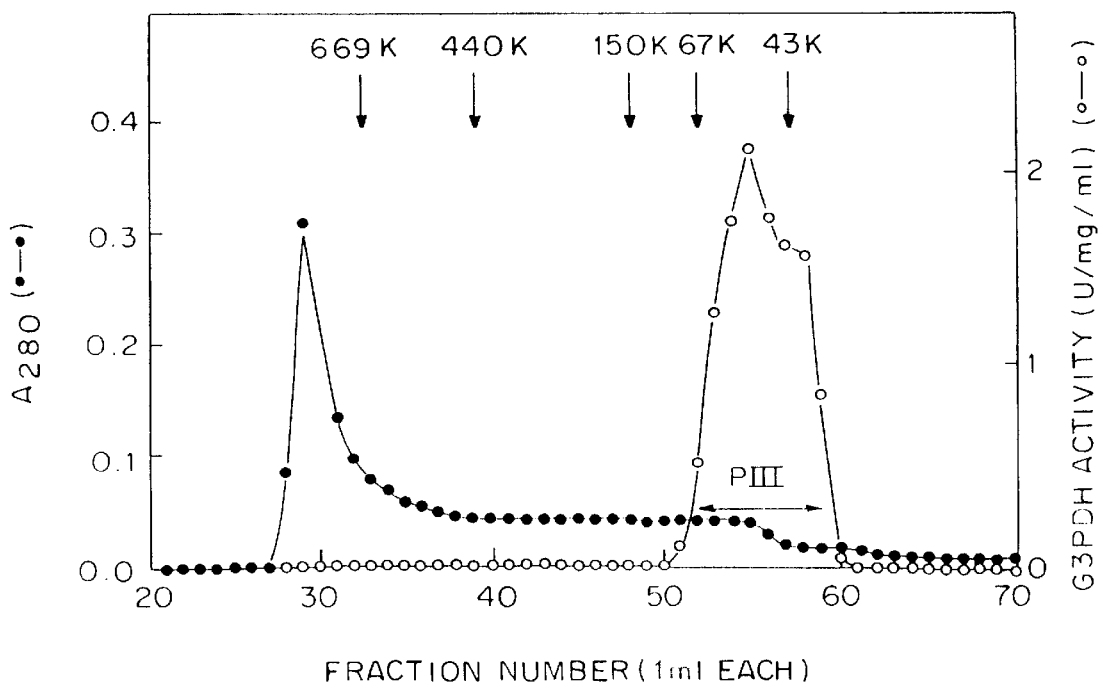

HepG2 CM concentrated by ultrafiltration and by ammonium sulfate precipitation was chromatographed on a heparin SEPHAROSE column as described in Example I. Adipogenic activity eluted in two peaks, $F_I$ and $F_{II}$. When heparin-SEPHAROSE fraction I was chromatographed on a SEPHACRYL S-300 column in 20 mM sodium phosphate buffer, pH 7.0, the adipogenic activity was eluted in two major peaks with an apparent molecular weight above 670 kDa and between 320 and 170 kDa (FIG. 3A). However, if Fraction I was treated with n-octyl-β-D-glucopyranoside (OG) (1% w/v) and sonicated prior to being applied to SEPHACRYL S-300 column equilibrated in 20 mM phosphate buffer pH 7.0 containing 0.4% CHAPS and 0.5M NaCl, the adipogenic activity was recovered in a single peak having a molecular weight of 50 kDa (FIG. 3B). If both large molecular weight peaks obtained by gel filtration chromatography in the absence of OG and CHAPS were treated with OG and CHAPS prior to rechromatographing on SEPHACRYL S-300, they were eluted as a single peak with an apparent molecular weight of 50 kDa. These results indicate that appearance of the high molecular weight forms of the HepG2-derived adipogenic factor were due to aggregation either of the adipogenic protein itself or of the adipogenic protein to other proteins. It is concluded that the free form of the adipogenic protein has an apparent molecular weight of 50 kDa. Stability studies indicated that the free 50 kDa form of the adipogenic protein is stable for three months at 4° C. in the presence of 0.4% CHAPS and 0.5M NaCl.

On the basis of the above results, a purification strategy of the adipogenic protein after treatment with OG and in the presence of CHAPS was designed.

Purification of an Adipogenic Protein in HePG2 CM

A. Solubilization of HepG2 low-molecular weight adipogenic factor

The fraction I obtained by a heparin-SEPHAROSE column was concentrated by an Amicon ultrafiltration system with a YM-30 membrane filter (Amicon Corp.). To the concentrated fraction I was added n-octyl-β-D-glucopyranoside (OG) (Sigma Chemical Co.) to achieve a final protein concentration of 10 mg/ml and an OG concentration of 1% (w/v). The mixture was incubated at 0° C. for 10 min. The ratio of OG/protein (w/w) was 1.0. After incubation, the mixture was sonicated four times at 20 KH (power: 20W-40%) for 30 sec under cooling condition by a sonicator (Model VC-40, Sonics & Materials, Inc., Danbury, Conn.) and subjected to molecular-sieve chromatography.

B. Molecular-sieve chromatography

Molecular-sieve chromatography of the protein, termed HepG2 low molecular weight adipogenic factor (HepG2 L-AF) was carried out on a SEPHACRYL S-300 HR column (4.4×68 cm) (Pharmacia-LKB) equilibrated with 20 mM sodium phosphate buffer, pH 7.0 containing 0.5M NaCl and 0.4% (w/v) 3-[(3-cholamidopropyl)-dimethylammonio]-1-propane sulfonate (CHAPS) (Sigma Chemical Co.). The solubilized sample (15 ml) was applied to the column and developed with the same buffer at a flow rate of 70 ml/hr. The eluate was collected in 10 ml fractions. Fractions having adipogenic activities were combined, filtered through a Millex GV filter (0.22 μm, Millipore) and stored at 4° C. for further purification. Most of adipogenic activity was recovered in a region of Mr of about 50 kDa.

C. Ion exchange chromatography

The 50 kDa fraction was dialyzed against 20 mM sodium phosphate buffer, pH 7.0 at 4° C. overnight using dialysis tubing with a MW cut off of 3500 (Spectrum Medical Industries, Inc., Califorina). OG was added to the dialyzed sample to a final concentration 0.5% (w/v) and the mixture was sonicated six times at 20 KHZ (power: 20 W-40%) for 10 sec under cooling conditions by a sonicator as described above.

The solubilized sample was subjected to anion-exchange chromatography on a MONO Q column (0.5×5.0 cm) (Pharmacia-LKB) equilibrated with 20 mM sodium phosphate buffer, pH 7.0, containing 0.8% (w/v) CHAPS, at a flow rate 0.5 ml/min. After washing the column with the same buffer, material having adipogenic activity was eluted with a linear gradient of NaCl from 0 to 0.25M in the same buffer (20 ml). The eluate was collected in 1 ml fractions.

Adipogenic activity was shown to elute with 0.16M NaCl (MONO Q fraction) (FIG. 4).

D. Reversed-Phase high performance liquid chromatography (RP-HPLC)

RP-HPLC was carried out on a VYDAC C4 column (0.46×25 cm) (The Separations Group, Califorina) .equilibrated with 0.05% (v/v) trifluoroacetic acid (TFA) in water (solution A). The MONO Q fraction was applied to the C4 column at a flow rate of 1 ml/min. After washing the column with solution A, adipogenic activity was eluted with a linear gradient of 0–50% acetonitrile in solution A (50 ml). The eluate was collected in 1 ml fractions to which 50 μl of 0.5M sodium phosphate buffer, pH 7.5 and 20 μl of 20% (w/v) CHAPS were added for neutralization. Acetonitrile was removed by evaporation using a Speedvac concentrator (Savant Instruments, New York). Water was added to the concentrated fraction to yield a final volume of 1 ml.

Adipogenic activity was shown to elute with about 37% acetonitrile (FIG. 5). The biochemical characteristics of the HepG2 adipogenic protein termed HepG2 L-AF are summarized in Table 3 and the purification is summarized in Table 4, below.

TABLE 3

Biochemical Properties of Adinogenic Protein, HepG2 L-AF

| | |
|---|---|
| Molecular weight (Molecular-sieve chromatography) | 50 kDa |
| Treatment | Relative Adipogenic Activity (%) |
| None | 100 |
| Heat 100° C., 10 min | 78 |
| DTT 10 mM, r.t., 1.5 hr | 60 |
| DTT 30 mM, r.t., 1.5 hr | 34 |
| pH 3 | 129 |
| pH 5 | 109 |
| pH 7 | 100 |
| pH 9 | 78 |
| pH 11 | 146 |
| TFA 0.25% (pH 2.0), r.t., 1 hr | 105 |
| TFA 0.25% (pH 2.0), r.t., 3 hr | 100 |
| Acetonitrile 20%, r.t., 3 hr | 85 |
| Acetonitrile 50% | 60 |

E. Molecular Weight Characterization by molecular sieve HPLC using a SPHEROGEL TSK 2000 SW column HepG2 L-AF (4.4 ml containing 0.4% (w/v) CHAPS) was obtained by R-HPLC as described above and concentrated to 230 μl using a microconcentrator (Ultrafree-MC, Millipore, MW cutoff: 10 kDa). The concentrate was sonicated 3 times (power: 20 W, 40%) for 5 seconds under cooling conditions using a sonicator (Model VC-40), SOnics and Materials, Inc., Danbury, Conn.), followed by centrifugation at 12,000 rpm for 10 minutes. The supernatant (190 μl) was applied to a SPHEROGEL TSK 2000 SW column (0.75×30 cm) (Altex) connected to a TSK SW guard column (0.75×7.5 cm) at a flow rate of 0.3 ml/min using 20 mM sodium phosphate buffer, pH 7.0, containing 0.1M $Na_2SO_4$ and 0.5% (w/v) CHAPS. The fractions (0.3 ml each) were mixed with 3 μl of bovine serum albumin (RIA grade, Sigma) at 10 mg/ml and filtered through a Millex GV4 filter (Millipore). The filtrate (40 μl) was assayed for adipogenic activity.

Figure 6:
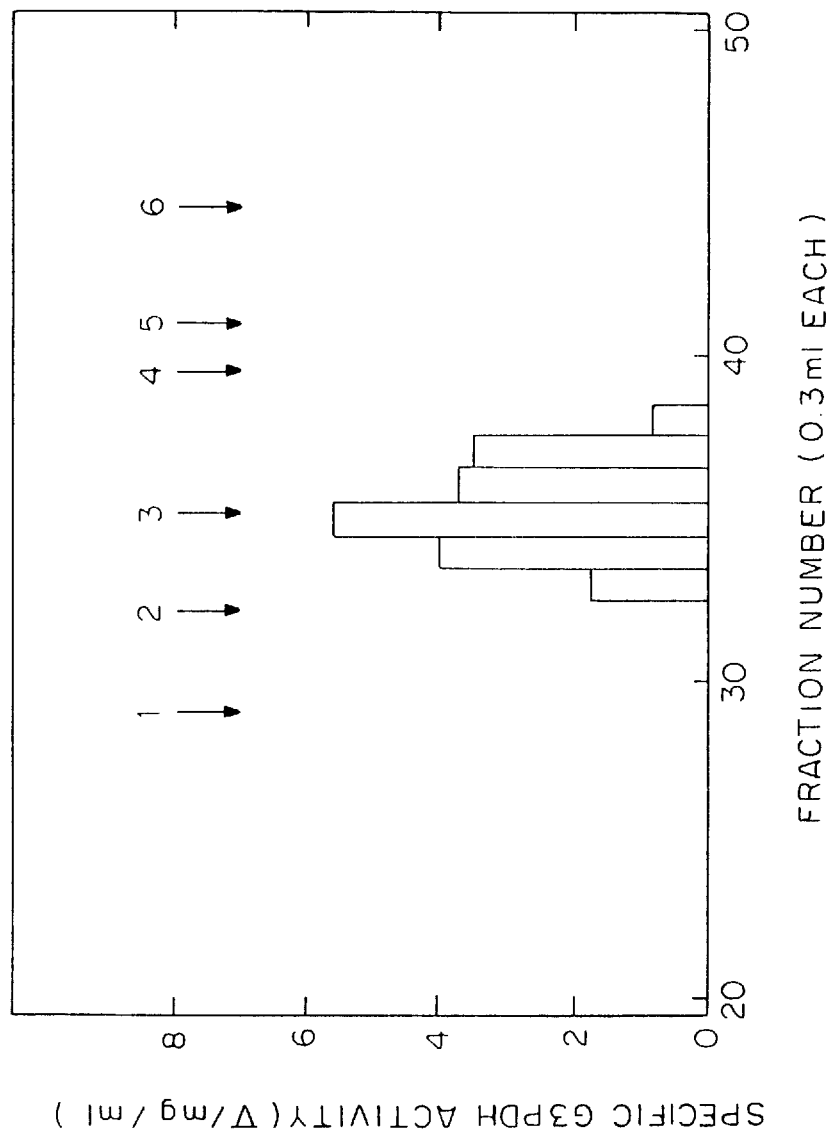
FIG. 6 shows the results of molecular sieve HPLC of HepG2 L-AF on a SPHEROGEL TSK 2000 column.
Figure 7:
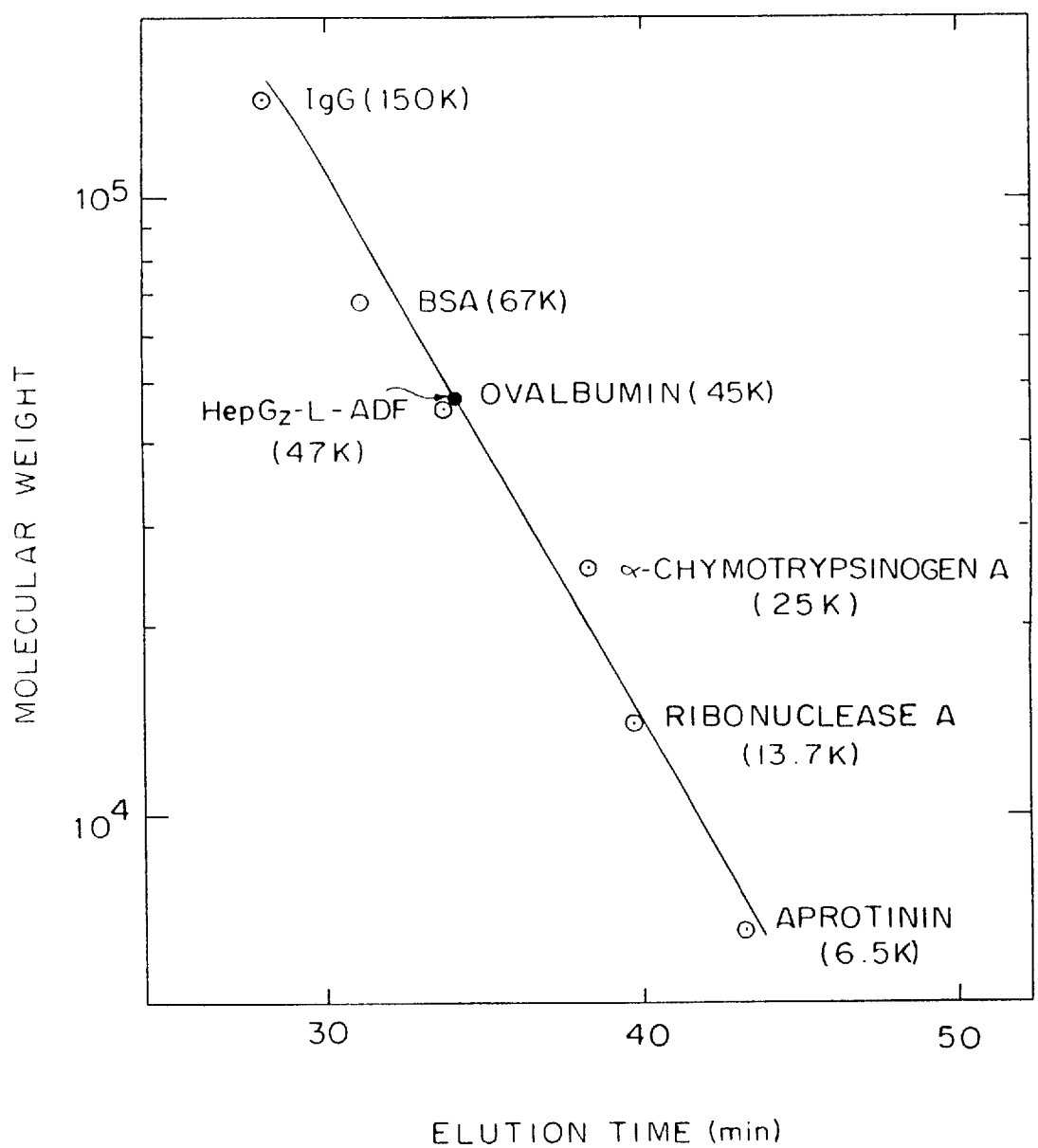
FIG. 7 is a graph showing the estimated molecular weight of HepG2 L-AF by molecular-sieve HPLC on a SPHEROGEL TSK 2000 SW column. Indicated are the molecular weights in kDa of several molecular weight markers: IgG (150), BSA (67), ovalbumin (45), α-chymotrypsinogen A (25), ribonuclease (13.7) and aprotinin (6.5).

Results are shown in FIG. 6. Arrows 1–6 indicate the elution position, respectively, of six molecular weight markers (IgG (150), BSA (67), ovalbumin (45), α-chymotrypsinogen A (25), ribonuclease (13.7) and aprotinin (6.5)). FIG. 7 shows the same data graphed as a function of elution time. Based on these observations a molecular weight of 47 kDa was estimated. This result is in close agreement with the 50 kDa molecular weight based on SEPHACRYL S-300 chromatography, described above.

EXAMPLE III

INITIAL PURIFICATION AND CHARACTERIZATION OF BOVINE ADIPOGENIC FACTORS

Purification of bovine adipogenic factors

The starting point for purification of these factors is crude fetuin, prepared according to the method of Pedersen (*Nature* 154:575–576 (1944)). Three different procedures were used to purify the factors: (1) For routine purification, the crude fetuin was dialyzed against start buffer (25 mM imidazole-$CH_3COOH$, pH 7.4) and then loaded on a chromatofocusing polybuffer exchange column PBE 94 gel (sold by Pharmacia) that had been equilibrated with start buffer. Unbound proteins were washed out with the start buffer and collected in the "flow-through" fraction. Factor $F_I$ was present in the flow-through fraction. The column was then washed with polybuffer 96-$CH_3COOH$, pH 6.0 (purchased

TABLE 4

Summary for Purification of Adipocyte Protein, HepG2 L-AF from Conditioned Medium of HepG2 Cells

| Purification Step | Total Protein | *Total Activity | Specific Activity | Purification (-fold) | Yield (%) | Dose Required for Activity (μg/ml) |
|---|---|---|---|---|---|---|
| Conditioned medium | 18,100 | 50,800 | 2.81 | (1) | (100) | |
| 30–50% $(NH_4)_2SO_4$ fraction | 7,030 | 43,800 | 6.23 | 2.2 | 86 | |
| Heparin-SEPHAROSE Fraction I | 622 | 22,100 | 35.5 | 12.6 | 44 | 5–10 |
| SEPHACRYL S-300 HR | 13.9 1.34 | 2,043 | 147 | 52.3 | 29 | 1–2 |
| MONO Q | 0.075 0.055 | 38.5 | 513 | 183 | 12 | 0.3–0.6 |
| VYDAC C4 | 0.0015 | 22 | 14,700 | 5,230 | 10 | 0.01–0.03 |

*Adipogenic activity is expressed as G3PDH activity, calculated by subtracting activity in control culture (no addition) from that in the presence of the sample.

from Pharmacia, chemical composition undisclosed) and subsequently washed with 1.0M NaCl. Factor $F_{II}$ was eluted with 1.0M NaCl. (2) The procedure was as in (1) except that after collection of the flow-through fraction, a pH gradient (pH 9.0 to pH 7.0) made with polybuffer PB 94 was applied to the column. Proteins not eluted by the gradient were subsequently eluted with 1M NaCl. $F_I$ adipogenic activity eluted with the flow-through fraction (pI >9.0). $F_{II}$ eluted with 1M NaCl (pH <7.0).

$F_{II}$ was subsequently loaded on a heparin-SEPHAROSE column equilibrated with 20 mM phosphate buffer pH 7.0. The column was washed in a stepwise manner with 20 mM phosphate buffer pH 7.0, then with 0.3M NaCl in 20 mM phosphate buffer pH 7.0 and finally with 1M NaCl in phosphate buffer pH 7.0. $F_{II}$ was eluted with 1M NaCl. $F_{II}$ was subsequently loaded on lectin SEPHAROSE column equilibrated with 20 mM phosphate buffer, pH 7.0, containing 0.15M NaCl. The active fraction was eluted with 0.5M alpha-methyl mannoside, dialyzed against 20 mM phosphate buffer, pH 7.0, and then loaded on a MONO Q ion exchange column. Elution was performed with a NaCl gradient from 0.1M to 0.5M NaCl. The active fraction was chromatographed on a hydrophobic interaction phenyl SEPHAROSE column. Elution was performed with a descending gradient of NaCl. The $F_I$ fraction was loaded on a heparin SEPHAROSE column equilibrated with 20 mM phosphate buffer at pH 7.0. The active fraction was eluted with the same buffer containing 0.1M NaCl By gel filtration on SEPHACRYL S-300 equilibrated with 20 mM phosphate buffer pH 7.0 containing 0.1M NaCl, $F_I$ eluted with a molecular weight of 660 kDa. $F_{II}$ had an apparent molecular weight of 230 kDa based on SDS-PAGE analysis. These estimates of molecular weight were considered more reliable than the ones obtained by procedure (c) below.

The procedure resulted in $F_{II}$ having a specific activity 250 to 500-fold that of crude fetuin and 5% of the adipogenic activity of crude fetuin. It resulted in an $F_I$ preparation with a specific activity at least 10-fold that of crude fetuin.

(3) By gel filtration of crude fetuin on SEPHACRYL S-300 in 20 mM potassium phosphate, pH 7.4, the adipogenic activity eluted primarily in two distinct peaks. The factor (or group of factors) in the first peak, which contained molecules of apparent molecular weights greater than 669 kDA, was labeled $F_I$. The factor (or group of factors) in the second peak, which contained molecules with apparent molecular weights in the range 232 to 445 kDA, was labeled $F_{II}$. In addition, a minor activity eluted with an apparent molecular weight of 69 kDA. The majority of adipogenic activity in fetuin was contained in $F_{II}$.

Initial Characterization of bovine adipogenic factors

Biochemical characterization demonstrated that $F_I$ and $F_{II}$ are distinct factors. Bovine adipogenic factor, $F_I$, was found to have a pI >9.4, to be heat and alkaline labile, protease sensitive, and stable during treatment with 2-mercaptoethanol or acid. $F_{II}$ was found to have a pI <4.0, be heat and acid labile, protease sensitive and partially destroyed (about 50%) by treatment with 2-mercaptoethanol. It is possible that the adipogenic protein present in $F_{II}$ is similar to, or identical with, the HepG2 L-AF described above.

The impurities present in the $F_I$ and $F_{II}$ preparations may have contributed to a greater or lesser degree to the observed pI. Furthermore, the glycoprotein nature of these factors, and the possibility that other sugars or proteoglycans were present in the fractions, may also have contributed to the observed pI. The key point is the fact that two distinct adipogenic factors were discernible and capable of separation by chromatofocusing.

Comparison of bovine factors with other known bovine substances

Other factors have been isolated from crude fetuin: an acidic glycoprotein having a molecular weight of 69 kDa (Spiro, R. G. (1960) *J. Biol. Chem.* 235:2860–2869), also called Spiro fetuin, and a large molecular weight factor called embryonin similar to α2-macroglobulin (Saloman, D. S. et al. (1982) *J. Biol. Chem.* 257:14093–14101). These two factors were found by the present inventors not to have adipogenic activity in the G3PDH assay. These results are shown in Table 5, below.

TABLE 5

Adipogenic Activities of Pedersen Fetuin and Spiro Fetuin

| Sample | Conc (μg/ml) | Specific mU/mg | G3PDH Activity-fold increase |
|---|---|---|---|
| Background | — | 19.3 | (1) |
| Pedersen fetuin[1] | 250 | 249 | 13 |
|  | 500 | 441 | 23 |
| Spiro fetuin[1] |  |  |  |
| Preparation A[2] | 1 | 10.7 | <1 |
|  | 10 | 11.9 | <1 |
|  | 100 | * | * |
| Preparation B[3] | 1 | 23.7 | 1.2 |
|  | 10 | 23.8 | 1.2 |
|  | 100 | * | * |

[1]Pederson fetuin was obtained from Sigma. Spiro fetuin was obtained from GIBCO
[2]Preparation A: Spiro fetuin dissolved in PBS
[3]Preparation B: Spiro fetuin dissolved in PBS and dialyzed against 20 mM sodium phosphate buffer, pH 7.0, containing 0.15 M NaCl.
*At 100 μg/ml, Spiro fetuin before and after dialysis was cytotoxic; adipocyte differentiation could therefore not be determined.

Based on these results, it was concluded that a preparation known as "pure fetuin", or Spiro fetuin, a 69 kDa acidic glycoprotein, was not responsible for the minor adipogenic activity observed at 69 kDa. Furthermore, as discussed earlier, the adipogenic activity disclosed by Gaillard et al. (*Biochem. Biophys. Acta* 846:185–191 (1985)) was attributed by these authors to the "pure" fetuin. Because the bovine adipogenic factors described herein are clearly distinguishable from "pure fetuin," the adipogenic activity in the crude Pedersen fetuin as disclosed by Gaillard et al., and as described in Table 5, above, could not have been the same as the purified bovine adipogenic protein described herein (see below).

EXAMPLE IV

PURIFICATION AND CHARACTERIZATION OF LOWER MOLECULAR WEIGHT BOVINE ADIPOGENIC PROTEIN

The bovine adipogenic factor formed in the chromatofocusing flow through (CFFT) fraction of crude Pedersen fetuin, referred as $F_I$ above (pI >9.0;Mr >660 kDa; heat and alkaline labile; protease sensitive; acid-stable; stable to 2-mercaptoethanol) was further characterized. The high molecular weight form was found to be caused by aggregation with other proteins of crude Pedersen fetuin, most probably α2-macroglobulin and the acidic glycoprotein called fetuin, as described below.

Figure 8A:
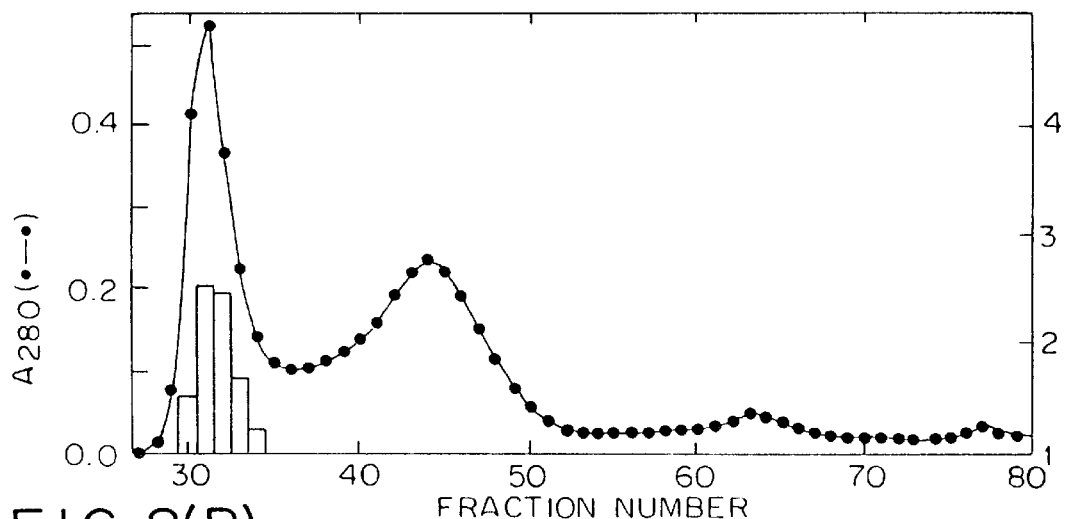
FIG. 8 shows the results of molecular-sieve chromatograph of chromatofocusing flow through (CFFT) fraction of crude Pedersen fetuin, and of its dissociated protein, on a SEPHAROSE CL6B column. CFFT (5.4 mg) was dissolved in 20 mM sodium phosphate buffer, pH 7.0 (PANEL A) or buffer containing 1% (w/v) OG (PANEL B) or 3% (w/v) OG (PANEL C). The resultant solutions (1.8 ml) were applied to a SEPHAROSE CL6B column in 20 mM sodium phosphate buffer, pH 7.0 containing 0.15M NaCl (PANEL A) or buffer containing 0.4% (w/v) CHAPS and 0.5M NaCl (PANELS B and C). Arrows 1–5 indicate the elution position of the Blue Dextran 2000 (2000 kDa), thyroglobulin (669 kDa), ferritin (445 kDa), bovine serum albumin (67 kDa) and α-chymotrypsinogen A (25 kDa), respectively.

The CFFT fraction was chromatographed on a SEPHAROSE CL6B column equilibrated in phosphate buffer, 20 mM, pH 7.4, in the presence of 0.5M NaCl (FIG. 8A). The majority of the activity was eluted in the void volume (MW >750 kDa). Western blot analysis of the high Mr fraction indicated the presence of α2-macroglobulin and the 60–40 kDa acidic glycoprotein fetuin. The results suggest that the adipogenic factor in the CFFT fraction was bound to, or aggregated with, other proteins such as α2-macroglobulin and acidic glycoprotein fetuin in a high molecular weight complex.

Figure 8B:
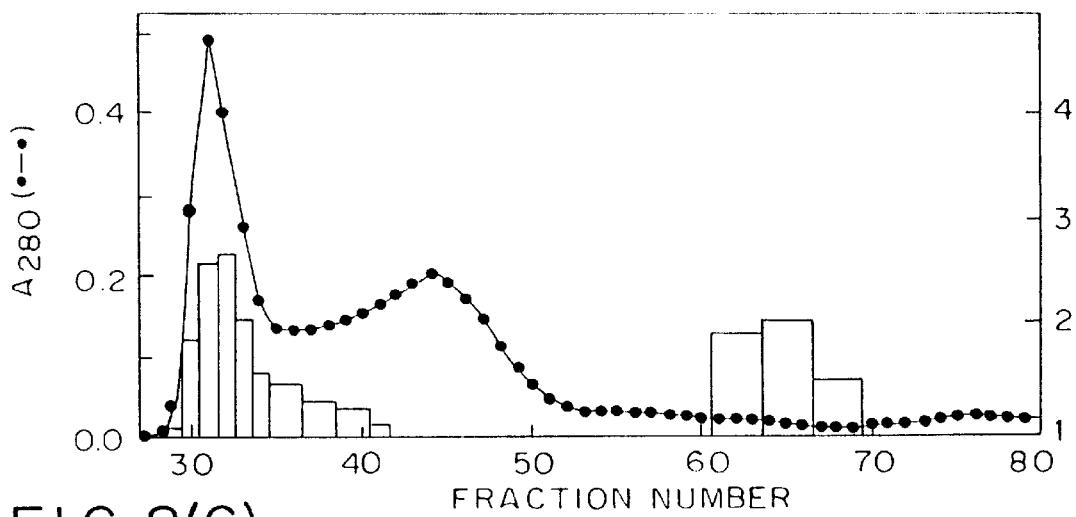
Figure 8C:
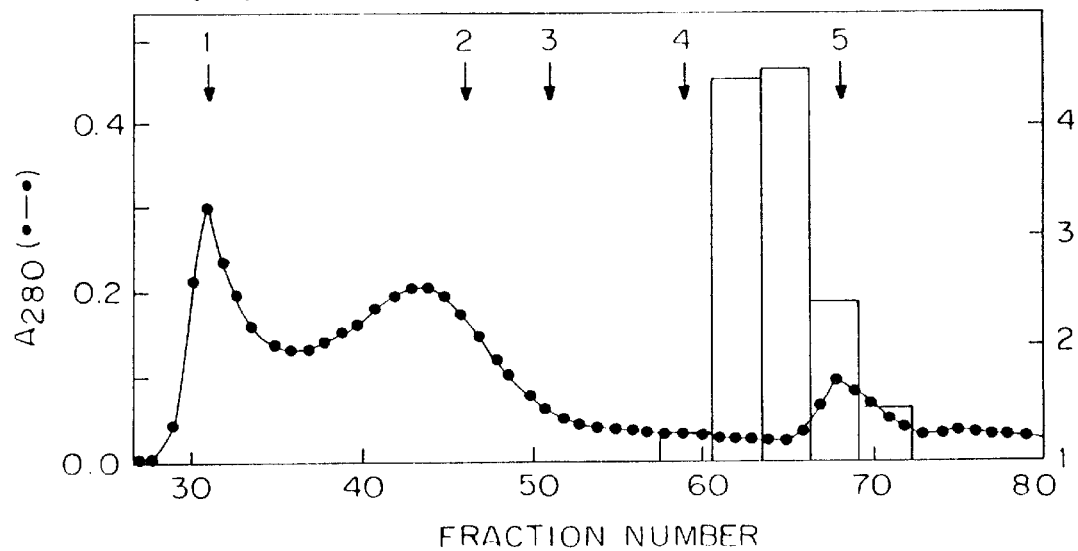
Figure 9:
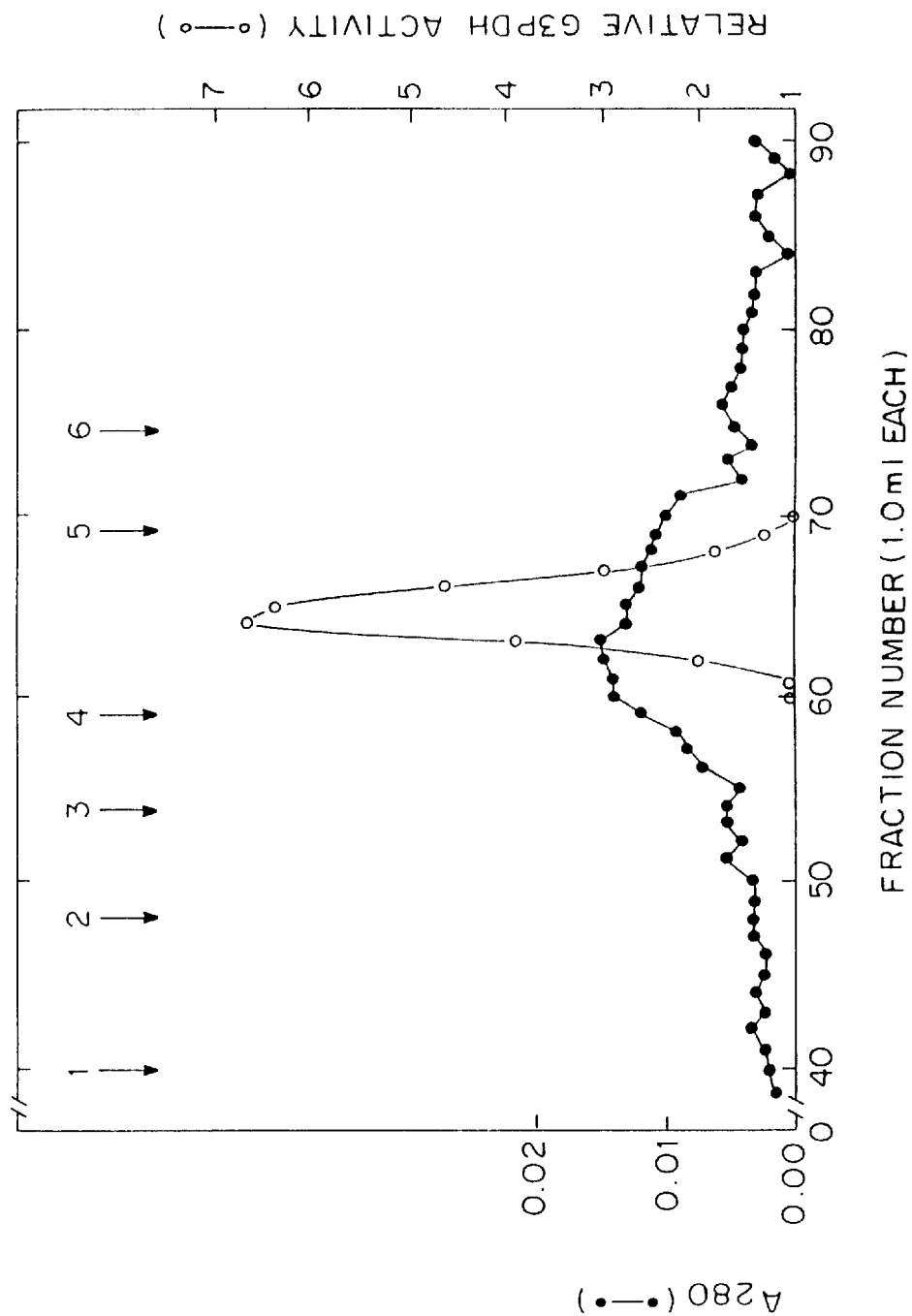
FIG. 9 shows the results of molecular-sieve chromatography of L-AF on SEPHACRYL S-200 to determine the molecular weight. L-AF (after SEPHAROSE CL6B chromatography) was concentrated by a Centricon-10 (Amicon) and applied to a SEPHACRYL S-200 HR column (1.6×50 cm) (Pharmacia) in 20 mM sodium phosphate buffer, pH 7.0 containing 0.4% CHAPS and 0.5M NaCl. The fractions (1.0 ml) were mixed with 10 μl of 10 mg/ml bovine serum albumin (RIA grade, Sigma) and then dialyzed against 20 mM sodium phosphate buffer, pH 7.0 containing 0.15M NaCl, followed by assay of adipogenic activity. G3PDH activity in control culture (no addition) was 27.7 mU/mg protein. Arrows 1–6 indicate the elution position of Blue Dextran 2000 (2000 kDa), IgG (150 kDa), bovine serum albumin (67 kDa), ovalbumin (43 kDa), α-chymotrypsinogen A (25 kDa) and ribonuclease A (13.7 kDa), respectively.

To prove this, CFFT was treated with the non ionic detergent n-octyl, β-D-glucopyranoside (OG) and with 3-[(3-cholamidopropyl)-dimethylammonio]-1-propane sulfonate (CHAPS) which is a nondenaturing Zwitterionic detergent. CFFT fraction was treated either with 1% OG (FIG. 8B) or 3% OG (FIG. 8C), followed by sonication and incubation at 0° C. for 30 min. The material was then chromatographed on SEPHAROSE CL6B equilibrated in 20 mM phosphate buffer, pH 7.4, containing 0.4% CHAPS and 0.5M NaCl. Adipogenic activity eluted as a single peak with a Mr <50 kDa. Solubilized CFFT (as described above) was chromatographed on SEPHACRYL S-200 to estimate its molecular weight more precisely (FIG. 9). The adipogenic protein eluted as a single peak with an apparent molecular weight of 34 kDa. This low molecular weight adipogenic protein was free of α2-macroglobulin and pure acidic glycoprotein fetuin.

These results prove that the high molecular weight CFFT adipogenic protein was a result of protein aggregation. The free form of the adipogenic protein is a 34 kDa protein. This low molecular weight adipogenic factor which has been solubilized from CFFT fraction is referred to as L-AF.

Isoelectric point of solubilized L-AF

Figure 10:
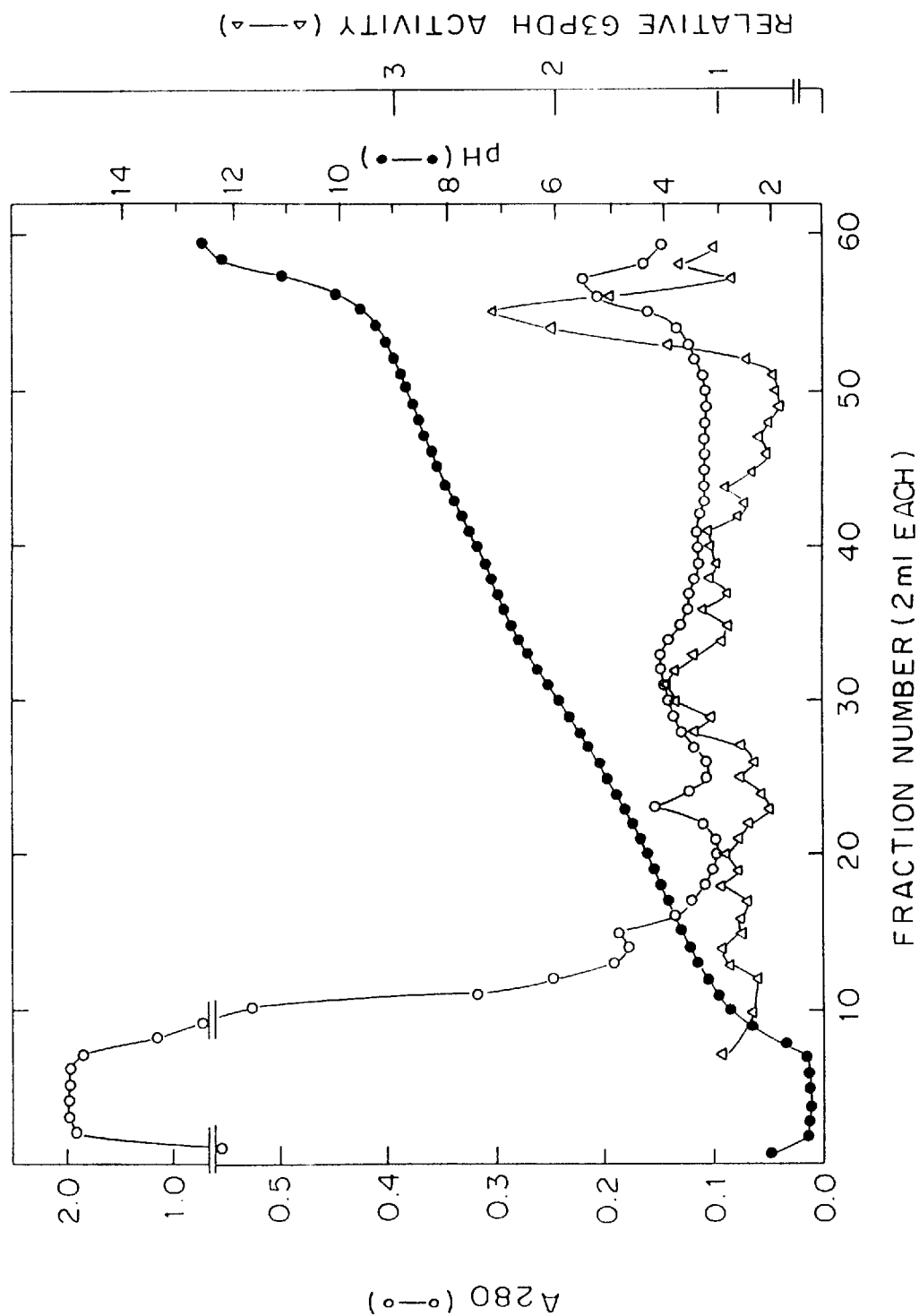
FIG. 10 shows the results of isoelectric focusing of L-AF.

The solubilized CFFT fraction was subjected to isoelectric focusing (FIG. 10). Measurement of the adipogenic activity of the eluted fractions indicated the presence of a single peak of activity with a pI of 9.6. This pI is quite different from the pI's of the two major proteins found in crude Pedersen fetuin, α2-macroglobulin (Mr=750 kDa, pI=5.2)) and acidic glycoprotein fetuin (Mr=48 kDa, pI=4.5).

To summarize, the biochemical properties of the L-AF obtained from bovine serum, the L-AF protein has an apparent molecular weight of about 34 kDa, a pI of 9.6, is heat unstable, is stable at a pH between pH 4.0 and pH 8.0 (see FIG. 11), and is resistant to treatment with 1 mM DTT.

Purification of the Low Molecular Weight Adipogenic Activity

A. Chromatofocusing of Pedersen fetuin

Fetuin (10 g) (Sigma Chemical Co., St. Louis, Mo.) was dissolved in 400 ml of 25 mM imidazole-HCl buffer, pH 8.0 and dialyzed against the same buffer at 4° C. overnight, followed by centrifugation at 10,000×g for 15 min. The supernatant was subjected to chromatofocusing on a polybuffer exchanger (PBE 94) column (bed vol=220 ml) (Pharmacia Fine Chemicals, Uppsala, Sweden) equilibrated with the same buffer. The changed column was washed with the same buffer. The effluent was dialyzed against 20 mM sodium phosphate buffer, pH 7.0 and stored at -20° C. until use. The recovery of protein in the effluent was 7.2%. Before solubilization, the effluent thus obtained was concentrated by an Amicon ultrafiltration system with a YM-10 membrane filter (Amicon Corp., Massachusetts) and centrifuged at 40,000×g for 1 hr.

B. Solubilization of L-AF from CFFT

CFFT was dissolved in 20 mM sodium phosphate buffer, pH 7.0, OG to yield a final concentrations of 5 mg/ml protein and 3.0% OG (w/v), and was then incubated at 0° C. for 15 min. The ratio of OG/protein (w/w) was 6.0. After incubation, the mixture was sonicated four times at 20 KHZ (power: 20 W-40%) for 30 sec under cooling conditions, as described above and subjected to ion exchange chromatography.

C. Ion exchange chromatography

Fetuin L-AF was carried out in a S-SEPHAROSE fast flow column (1×11.5 cm) (Pharmacia-LKB) equilibrated with 20 mM sodium phosphate buffer, pH 7.0, containing 0.8% (w/v) CHAPS. The solubilized sample was applied to the column at a flow rate of 1 ml/min. After washing the column with the same buffer, adipogenic activities were eluted with a linear gradient of NaCl (0 to 0.2M) in the same buffer (180 ml). The eluate was collected in 5 ml fractions.

Adipogenic activity eluted with 60 mM NaCl (SEPHAROSE fraction).

D. RP-HPLC

RP-HPLC was carried out on a VYDAC C4 column (0.46×25 cm) (The Separations Group, Massachusetts) equilibrated with 0.05% (v/v) trifluoroacetic acid (TFA) in water (solution A). The S-SEPHAROSE fraction was applied to the C4 column at a flow rate of 1 ml/min. After washing the column with solution A (15 ml), and with a linear gradient of acetonitrile concentration from 0 to 27% (v/v) in solution A (15 ml), adipogenic activity was eluted with a linear gradient of acetonitrile concentration from 27 to 42% in solution A (50 ml), followed by washing with 100% acetonitrile containing 0.05% TFA. The eluate was collected in 1 ml fractions to which 50 μl of 0.5M sodium phosphate buffer, pH 7.5 and 20 μl of 20% (w/v) CHAPS were added for neutralization; acetonitrile was removed by evaporation using a Speedvac Concentrator (Savant Instruments, New York). Water was added to the concentrated fraction to make a final volume 1 ml. Adipogenic activity eluted with about 31% acetonitrile (FIG. 12).

Figure 11:
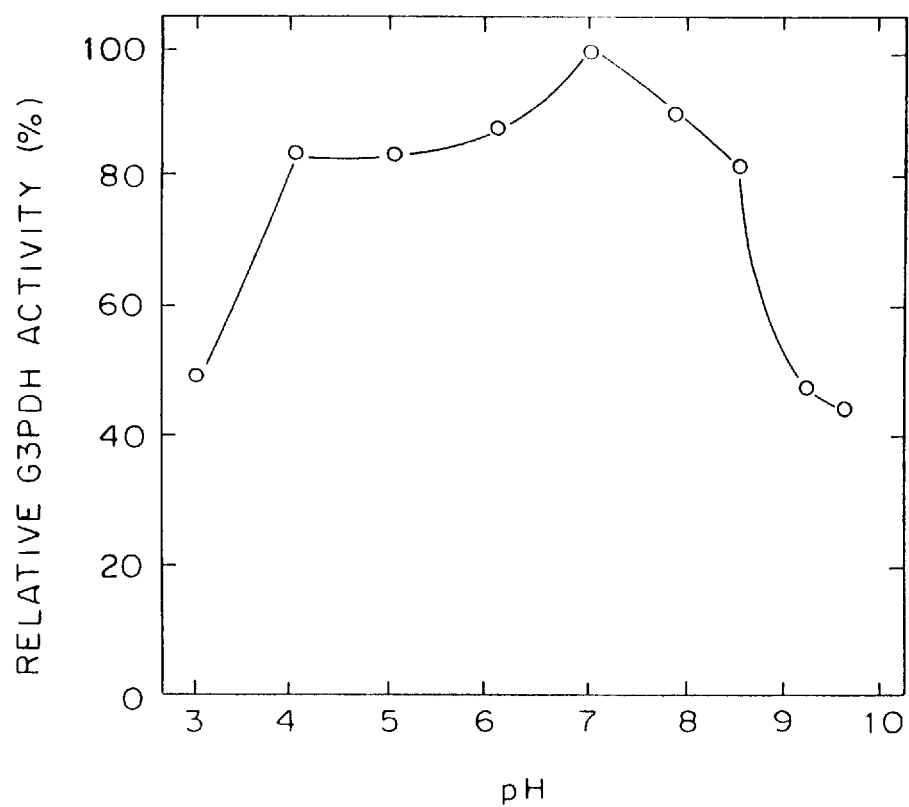
FIG. 11 is a graph showing the pH stability of L-AF. L-AF was dialyzed against 0.1M sodium citrate buffer containing 0.15M NaCl (pH 3–5), 0.1M sodium phosphate buffer containing 0.15M NaCl (pH 6–8), and 0.1M glycine-NaOH buffer containing 0.15M NaCl (pH 9–10) at 4° C. for 36 h. The resultant solution was dialyzed against 20 mM sodium phosphate buffer, pH 7.0 containing 0.15M NaCl at 4° C. overnight and then assayed for adipogenic activity. The values were expressed relative to the activity at pH 7.0 taken as 100%.

To summarize, the serum-derived adipogenic protein, L-AF, has a molecular weight of 34 kDa, a pI of 9.6. Its pH stability is shown in FIG. 11. Table 6 provides a summary of L-AF purification.

TABLE 6

Summary for Purification of Fetuin L-AF

| Purification Step | Total Protein | *Total Activity | Specific Activity | Purification (-fold) | Yield (%) | Dose Required for Activity (μg/ml) |
|---|---|---|---|---|---|---|
| Pedersen Fetuin | (75) | (144.6) | 1.93 | (1) | (100) | 200–300 |
| Chromatofocusing | (5.5) | (30.6) | 5.56 | 2.9 | 21.1 | 50–100 |
| S. SEPHAROSE FF | 0.247 | 25.7 | 104 | 53.9 | 10 | 1–3 |
| VYDAC C4 | 0.002 | 16.2 | 8100 | 4200 | 45 | 0.03–0.05 |

*Adipogenic activity is expressed as G3PDH activity, calculated by subtracting activity in control culture (no addition) from that in the presence of the sample.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A method for determining, in a human subject, the quantity of a protein which plays a role in the differentiation of fat cells, comprising:

removing a sample of a biological fluid or tissue from said subject; and measuring the amount of an adipogenic protein having an apparent molecular weight of about 50 kDa by molecular sieve gel filtration chromatography and which is obtainable from a HepG2 cell line, or an aggregate or complex of said protein, in said fluid or tissue.

2. A method for determining, in a human subject, the quantity of a protein which plays a role in the differentiation of fat cells, comprising:

removing a sample of a biological fluid or tissue from said subject; and measuring the amount of an adipogenic protein having an apparent molecular weight of about 34 kDa by molecular sieve gel filtration chromatography, a pI of 9.6, and stability to a pH of between about 4.0 and 8.0, or an aggregate or complex of said adipogenic protein, in said fluid or tissue.

* * * * *